United States Patent
Maruyama et al.

(10) Patent No.: US 7,987,723 B2
(45) Date of Patent: Aug. 2, 2011

(54) COPYING APPARATUS

(75) Inventors: Kensuke Maruyama, Tokyo (JP); Osamu Yamaguchi, Sagamihara (JP); Takashi Shimanuki, Yokohama (JP); Koichi Tsuji, Machida (JP); Takahiro Ikeda, Yokosuka (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 0 days.

(21) Appl. No.: 12/538,211

(22) Filed: Aug. 10, 2009

(65) Prior Publication Data

US 2009/0293620 A1 Dec. 3, 2009

Related U.S. Application Data

(63) Continuation of application No. PCT/JP2008/068896, filed on Oct. 17, 2008.

(30) Foreign Application Priority Data

Oct. 19, 2007 (JP) .................. 2007-272982

(51) Int. Cl.
*G01N 29/06* (2006.01)
(52) U.S. Cl. ........................ 73/633; 73/634
(58) Field of Classification Search ............. 73/633–634
See application file for complete search history.

(56) References Cited

U.S. PATENT DOCUMENTS

| 4,166,395 | A | * | 9/1979 | Dannehl | 73/634 |
|---|---|---|---|---|---|
| 5,568,527 | A | * | 10/1996 | Richardson et al. | 376/245 |
| 5,586,155 | A | * | 12/1996 | Erbes et al. | 376/249 |
| 5,661,242 | A | * | 8/1997 | Schreiner et al. | 73/623 |
| 6,220,099 | B1 | * | 4/2001 | Marti et al. | 73/633 |
| 6,904,817 | B2 | * | 6/2005 | Davis et al. | 73/865.8 |
| 7,134,352 | B2 | * | 11/2006 | Davis et al. | 73/865.8 |
| 7,587,942 | B2 | * | 9/2009 | Smith et al. | 73/622 |

FOREIGN PATENT DOCUMENTS

| JP | 61-96453 A | 5/1986 |
|---|---|---|
| JP | 61-134659 A | 6/1986 |
| JP | 63-119984 A | 5/1988 |
| JP | 6-242087 | 9/1994 |
| JP | 2007-160406 A | 6/2007 |

OTHER PUBLICATIONS

English translation of International Preliminary Report On Patentability for PCT/JP2008/068896, May 11, 2010.*

* cited by examiner

*Primary Examiner* — Hezron Williams
*Assistant Examiner* — Rose M Miller
(74) *Attorney, Agent, or Firm* — Oblon, Spivak, McClelland, Maier & Neustadt, L.L.P.

(57) ABSTRACT

There is provided a copying apparatus that copies a workpiece, includes a shoe that is brought into contact with the workpiece, an air cylinder that enables moving the shoe in a vertical direction, a clamping mechanism that grasps the workpiece from side surfaces placed in a direction orthogonal to a traveling direction and, and a lateral translatory slide guide that slides the clamping mechanism in the direction.

18 Claims, 30 Drawing Sheets

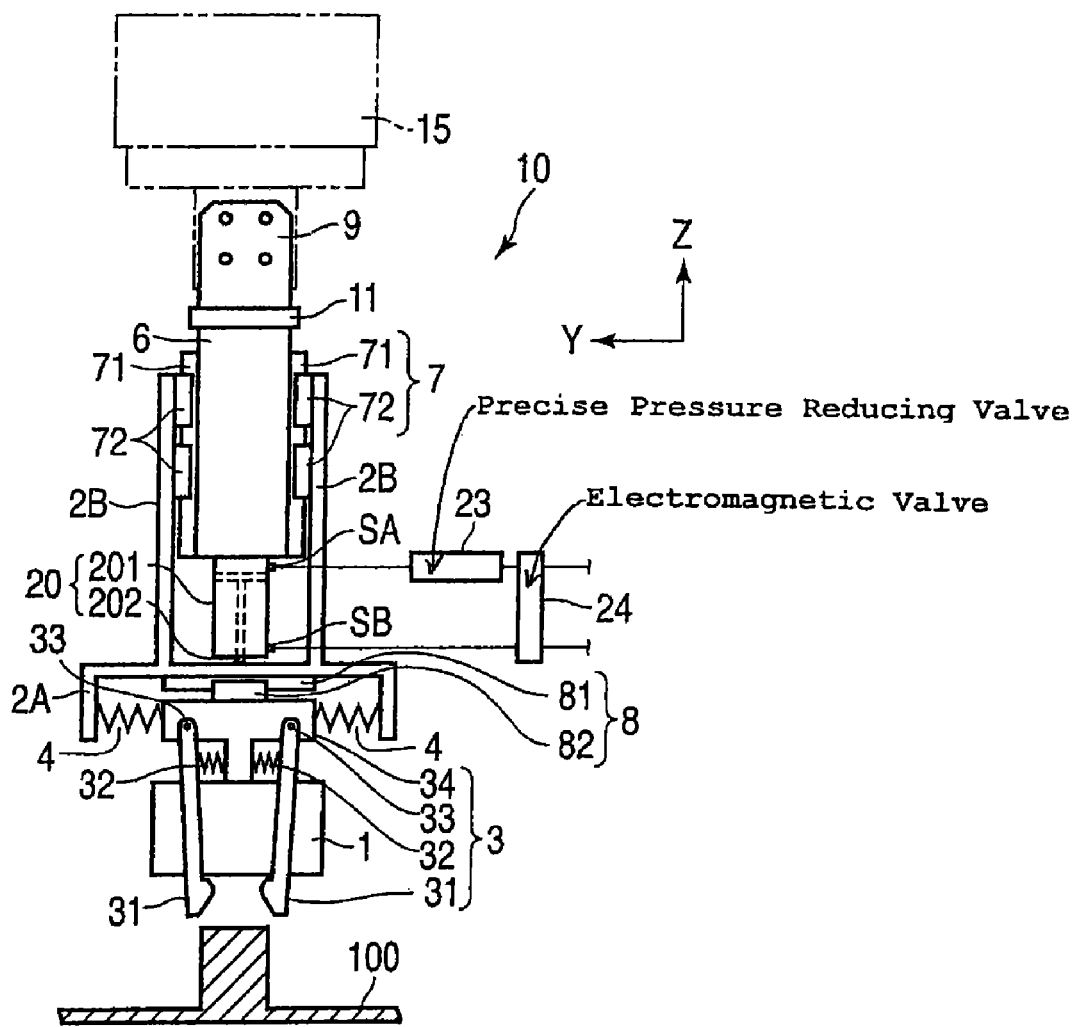
F I G. 1A

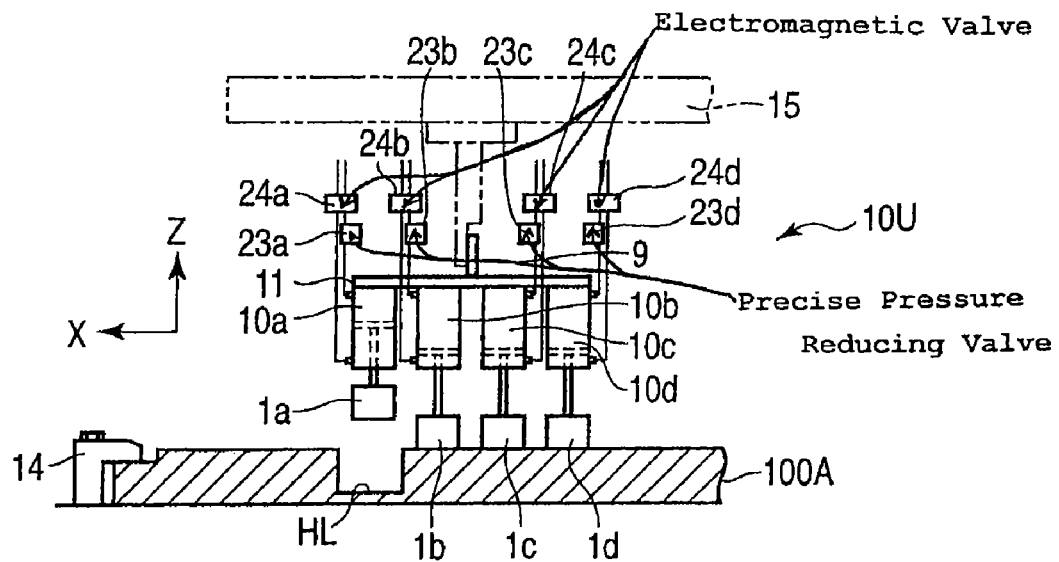
F I G. 4A
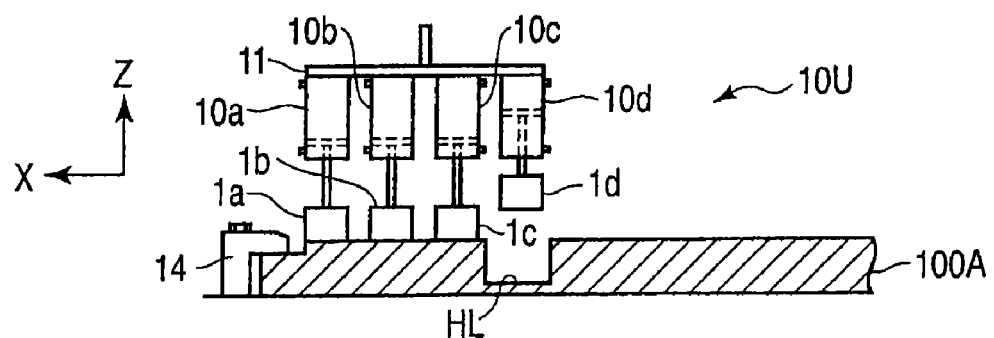
F I G. 4B

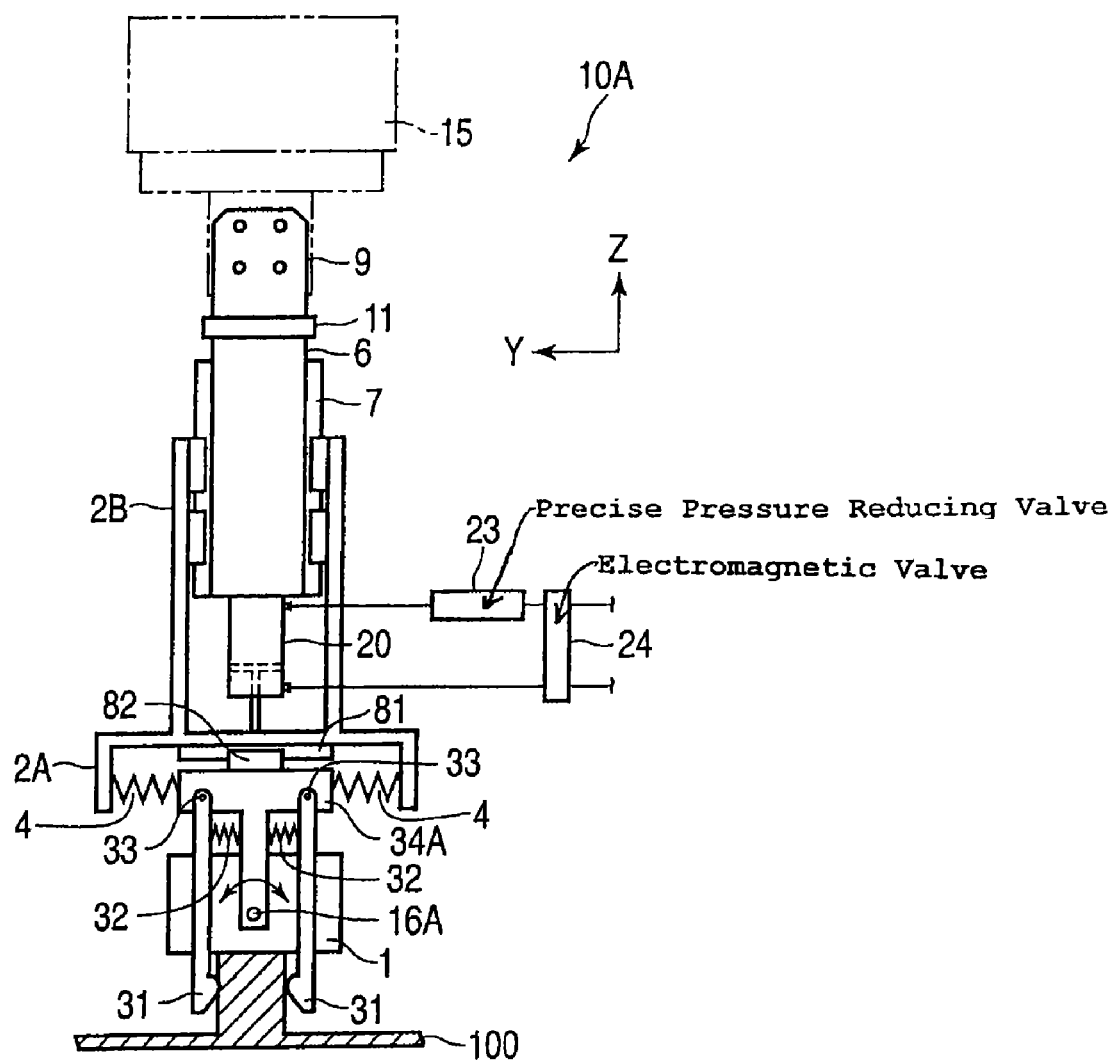
F I G. 5

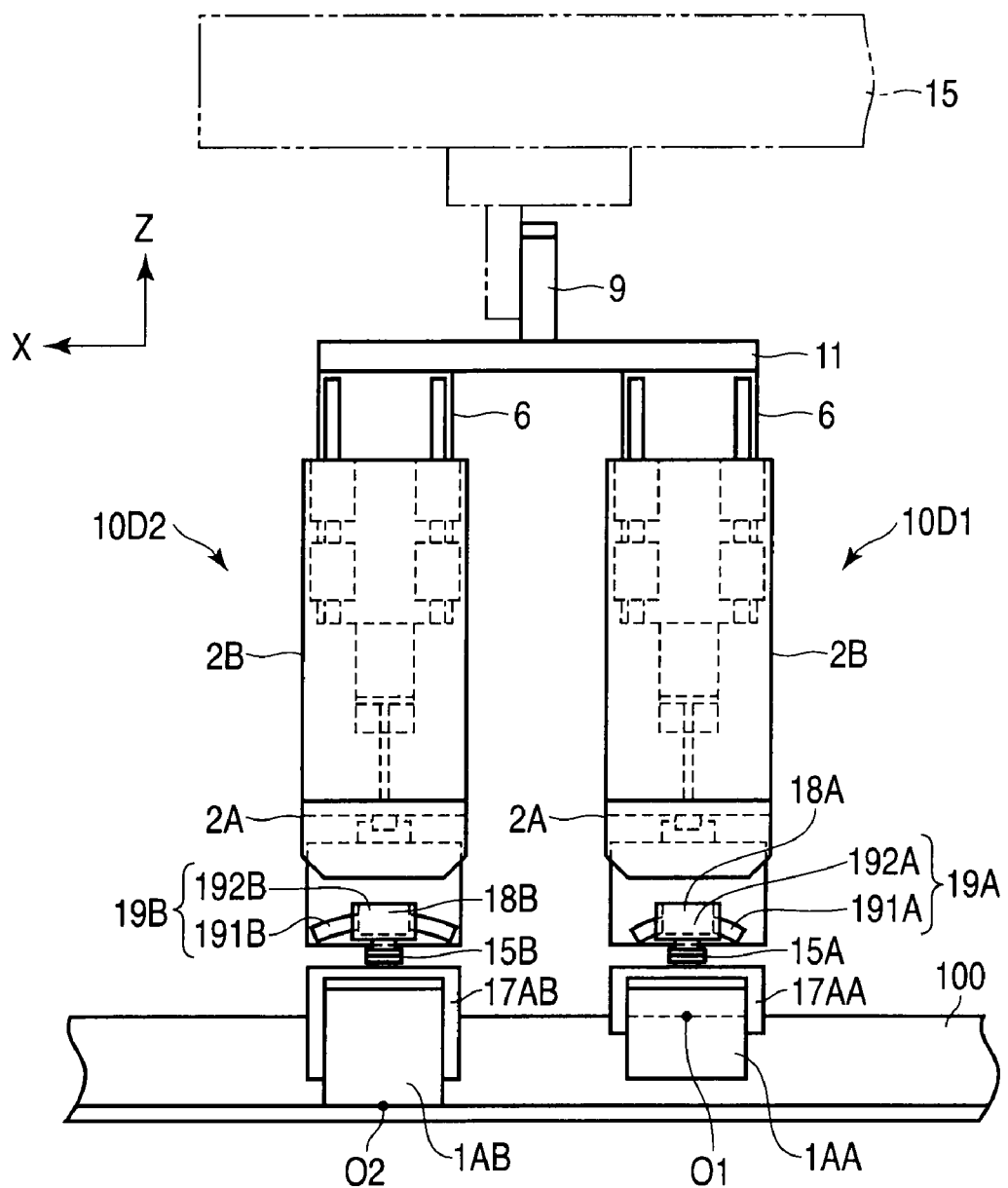
F I G. 9

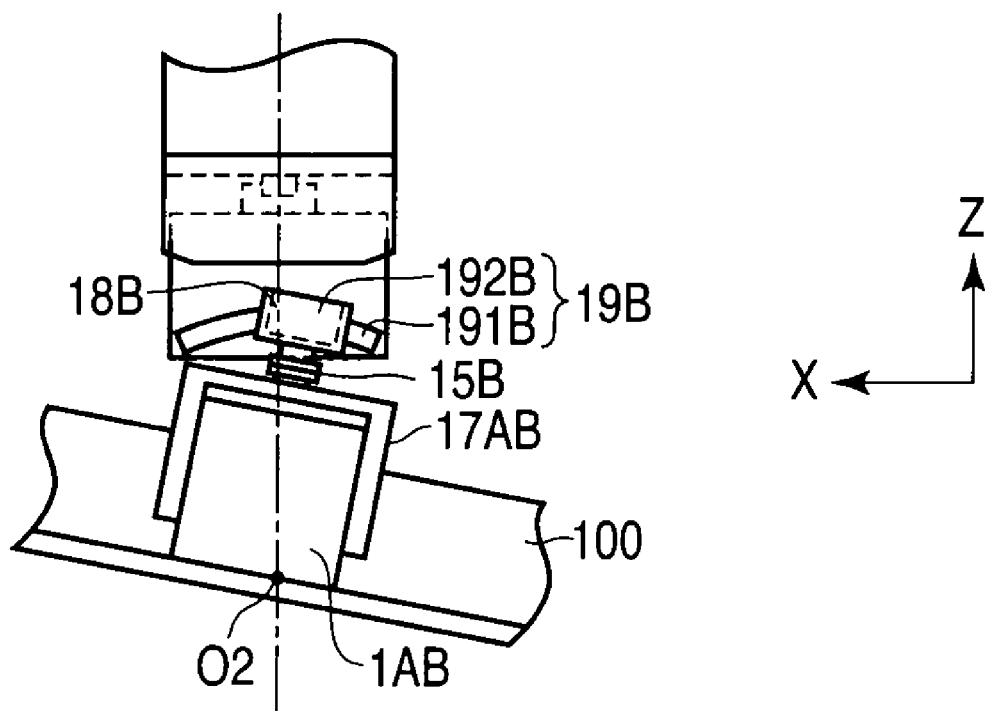
F I G. 10

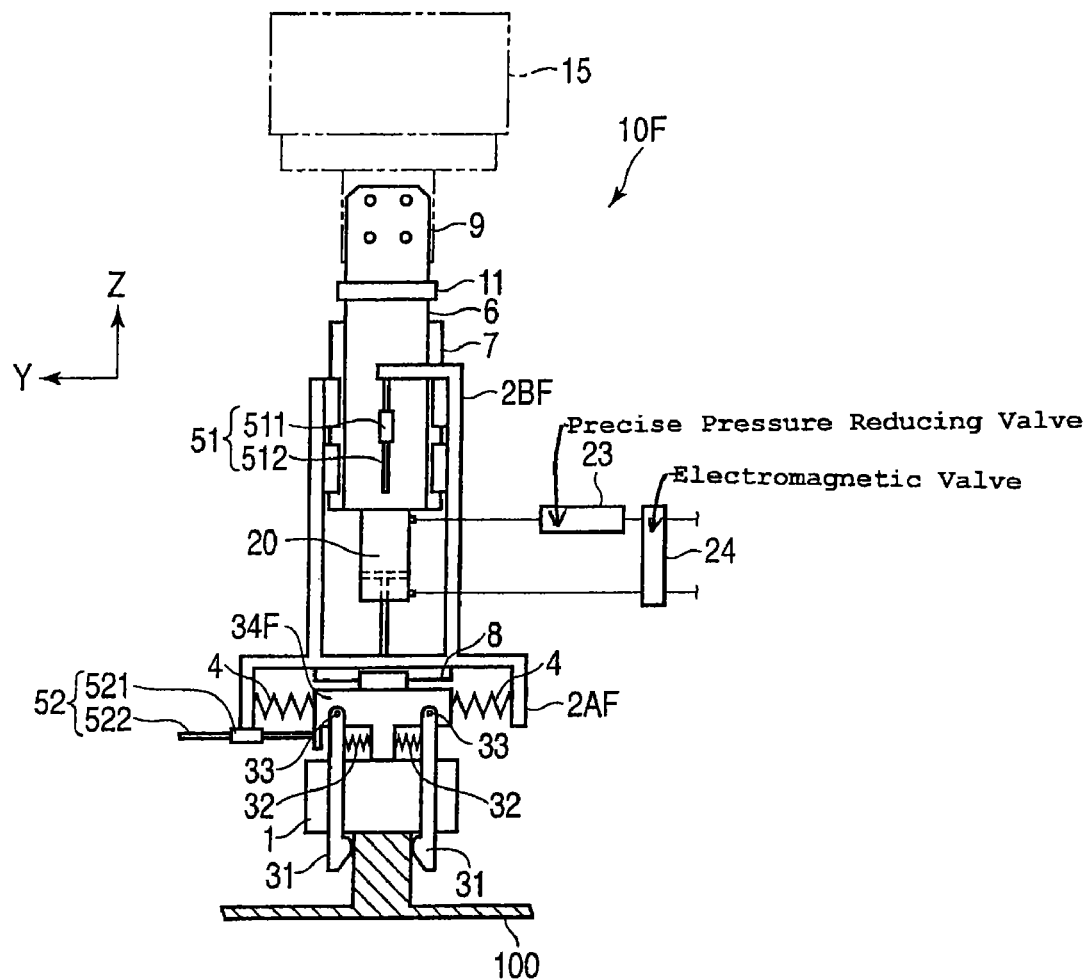
F I G. 12A

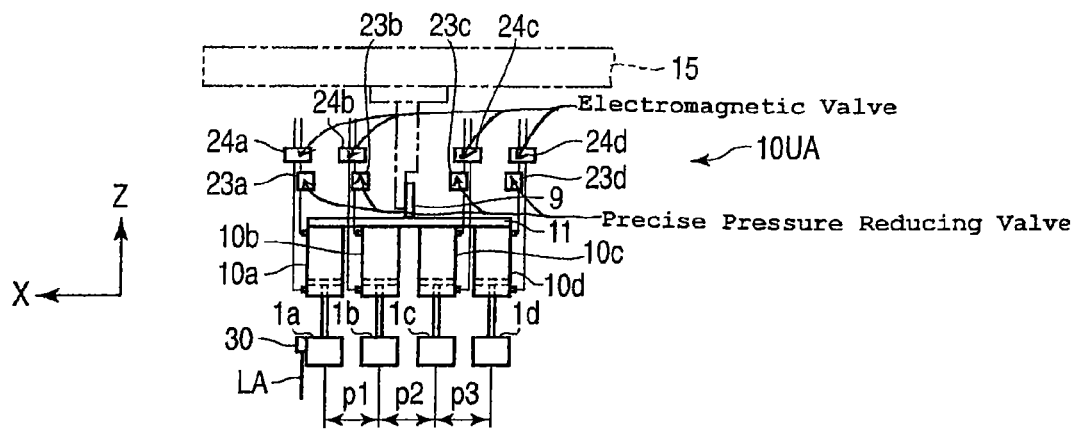
F I G. 13
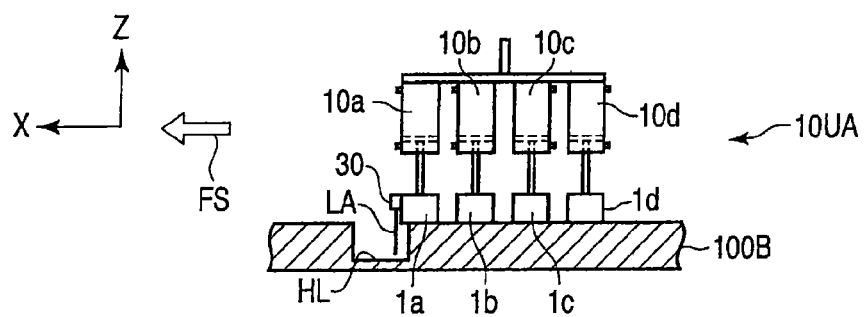
F I G. 14A

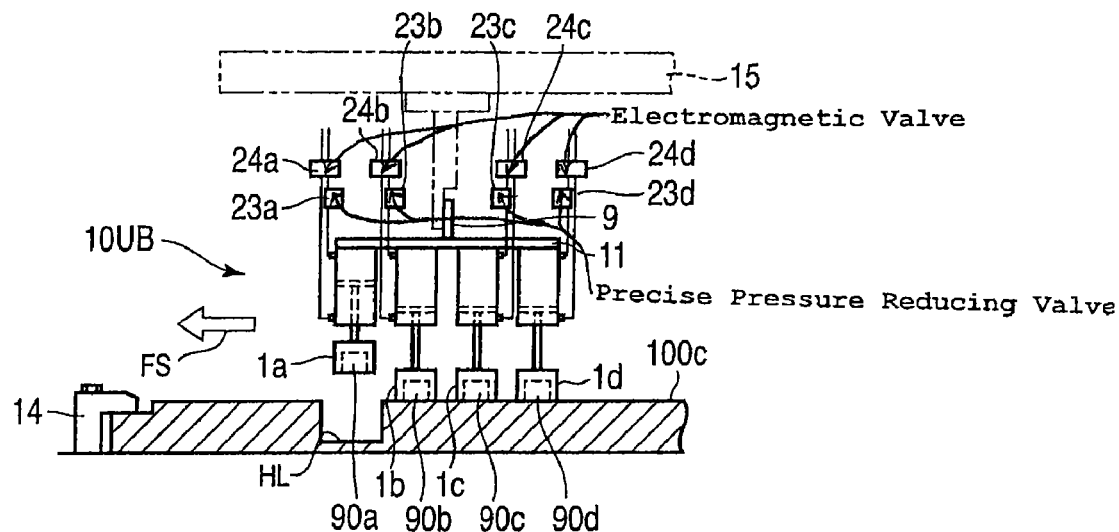
F I G. 15A
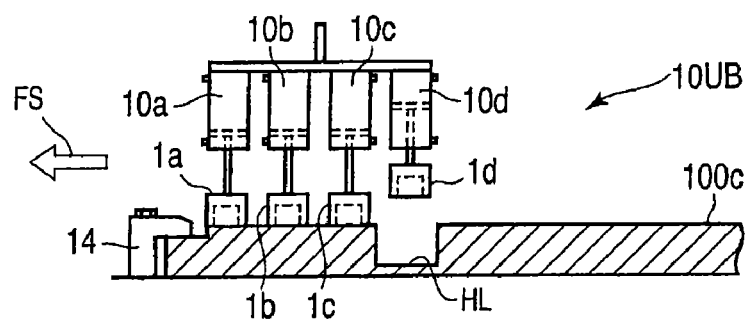
F I G. 15B

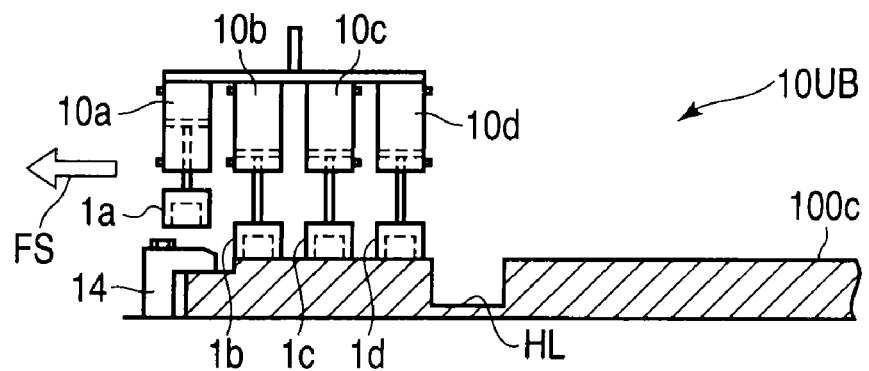
F I G. 15C
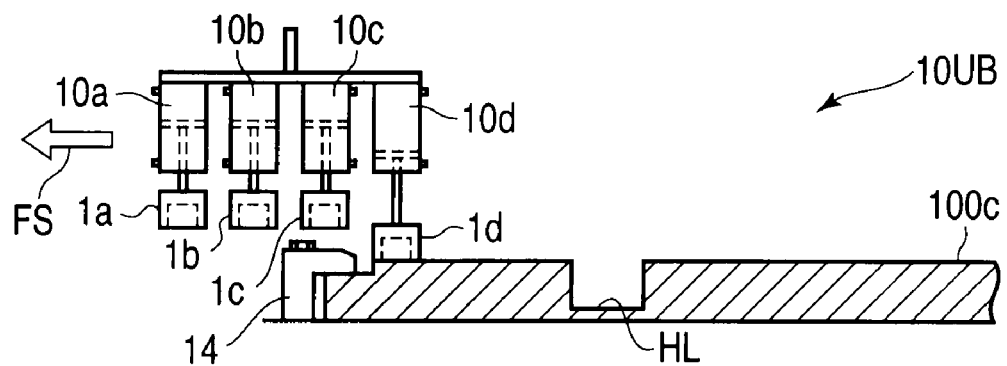
F I G. 15D

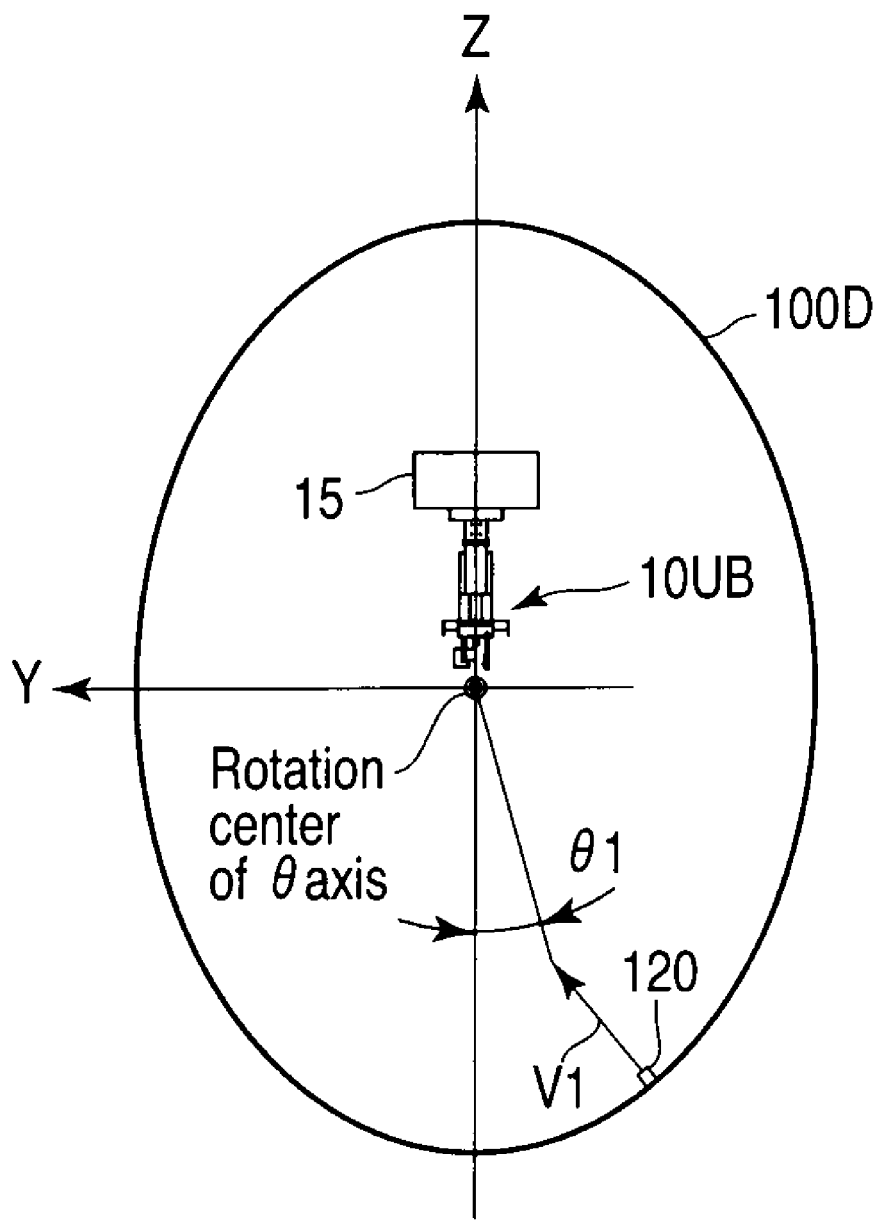
F I G. 21

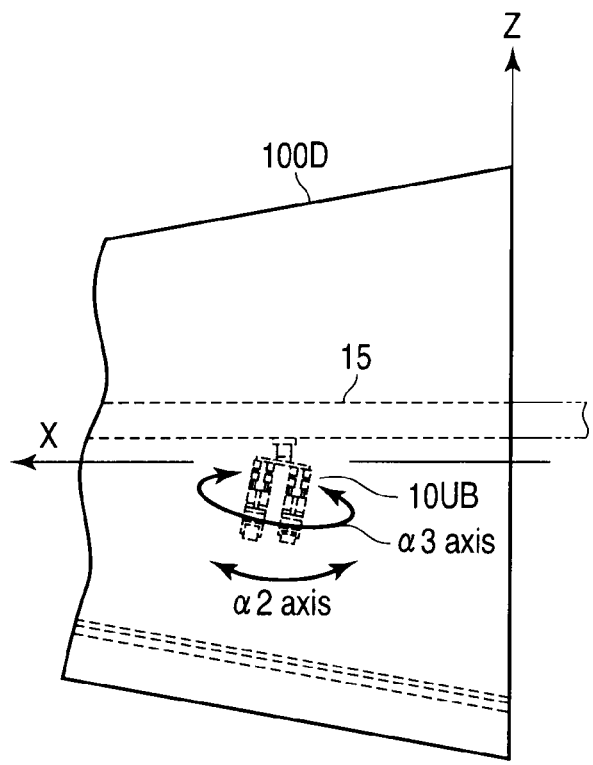
F I G. 26
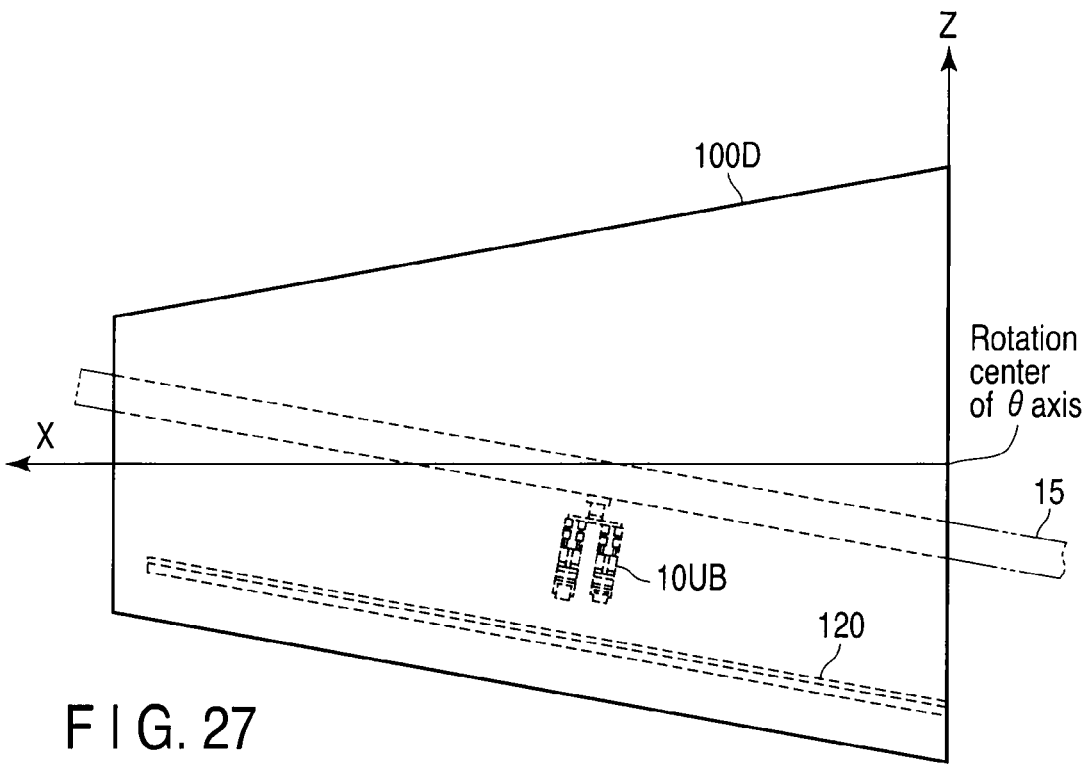
F I G. 27

COPYING APPARATUS

CROSS-REFERENCE TO RELATED APPLICATIONS

This is a Continuation Application of PCT Application No. PCT/JP2008/068896, filed Oct. 17, 2008, which was published under PCT Article 21(2) in Japanese.

This application is based upon and claims the benefit of priority from prior Japanese Patent Application No. 2007-272982, filed Oct. 19, 2007, the entire contents of which are incorporated herein by reference.

BACKGROUND OF THE INVENTION

1. Field of the Invention

The present invention relates to a copying apparatus that copies a shape of a workpiece.

2. Description of the Related Art

In general, in a field of, e.g., examination, measurement, or processing, a copying apparatus that copies a surface is used. A general copying apparatus performs a copying operation by pressing the copying apparatus against a workpiece or a dummy as a target (see, e.g., Jpn. Pat. Appln. KOKAI Publication No. 6-242087).

However, in a conventional copying apparatus, just pressing the copying apparatus against a workpiece cannot cope with a situation where an interferer, e.g., a discontinuous portion is present in a workpiece as a target. That is because the copying apparatus may be possibly fitted in the discontinuous portion to become unmovable or may possibly interfere with a jig that is used to fix the workpiece.

Such a discontinuous portion can be an interferer for the copying apparatus. As a workpiece having such a discontinuous portion, there is, e.g., a longeron provided in an airframe of an aircraft. This workpiece has a longitudinal protruding shape. Further, this workpiece has a complicated shape having not only a linear portion but also a curved portion.

BRIEF SUMMARY OF THE INVENTION

It is an object of the present invention to provide a copying apparatus suitable for copying a workpiece having a complicated shape with an interferer.

A copying apparatus according to an aspect of the present invention is a copying apparatus that copies a workpiece, comprising: a shoe that is brought into contact with the workpiece; an air cylinder that enables moving the shoe in a vertical direction; grasping means for grasping the workpiece from side surfaces with respect to a traveling direction in which the workpiece is copied; and sliding means for sliding the grasping means in a direction orthogonal to the traveling direction in which the workpiece is copied.

BRIEF DESCRIPTION OF THE SEVERAL VIEWS OF THE DRAWING

FIG. 1A is a constitutional diagram showing a state before a copying apparatus according to a first embodiment of the present invention grasps a workpiece;

FIG. 4A is a constitutional diagram showing a state of a first stage of a copying operation performed by the copying apparatus according to the first embodiment of the present invention;

FIG. 4B is a constitutional diagram showing a state of a second stage of the copying operation performed by the copying apparatus according to the first embodiment of the present invention;

FIG. 5 is a front view showing a structure of a copying apparatus according to a second embodiment of the present invention;

FIG. 9 is a side view showing a structure of two copying apparatuses according to the fifth embodiment of the present invention;

FIG. 10 is a constitutional diagram showing a state where a shoe of the copying apparatus according to the fifth embodiment of the present invention is inclined;

FIG. 12A is a front view showing a structure in an appropriate copying state of a copying apparatus according to a seventh embodiment of the present invention;

FIG. 13 is a side view showing a structure of a copying apparatus according to an eighth embodiment of the present invention;

FIG. 14A is a constitutional diagram showing a state of a first stage of a copying operation performed by the copying apparatus according to the eighth embodiment of the present invention;

FIG. 15A is a constitutional diagram showing a state of a first stage of a copying operation performed by a copying apparatus according to a ninth embodiment of the present invention;

FIG. 15B is a constitutional diagram showing a state of a second stage of the copying operation performed by the copying apparatus according to the ninth embodiment of the present invention;

FIG. 15C is a constitutional diagram showing a state of a third stage of the copying operation performed by the copying apparatus according to the ninth embodiment of the present invention;

FIG. 15D is a constitutional diagram showing a state of a fourth stage of the copying operation performed by the copying apparatus according to the ninth embodiment of the present invention;

FIG. 21 is a constitutional diagram showing a state of the copying apparatus for explaining a procedure 1 in the ultrasonic flaw detection method according to the 10th embodiment of the present invention;

FIG. 26 is a constitutional diagram showing a state of the apparatus in axial rotation on an $\alpha 2$ axis and an $\alpha 3$ axis in the ultrasonic flaw detection method according to the 10th embodiment of the present invention; and FIG. 27 is a constitutional diagram showing a state where a posture of a feeder is inclined in an X axis direction in the ultrasonic flaw detection method according to the 10th embodiment of the present invention.

DETAILED DESCRIPTION OF THE INVENTION

Embodiments according to the present invention will now be described hereinafter with reference to the drawings.

First Embodiment

Figure 1B:
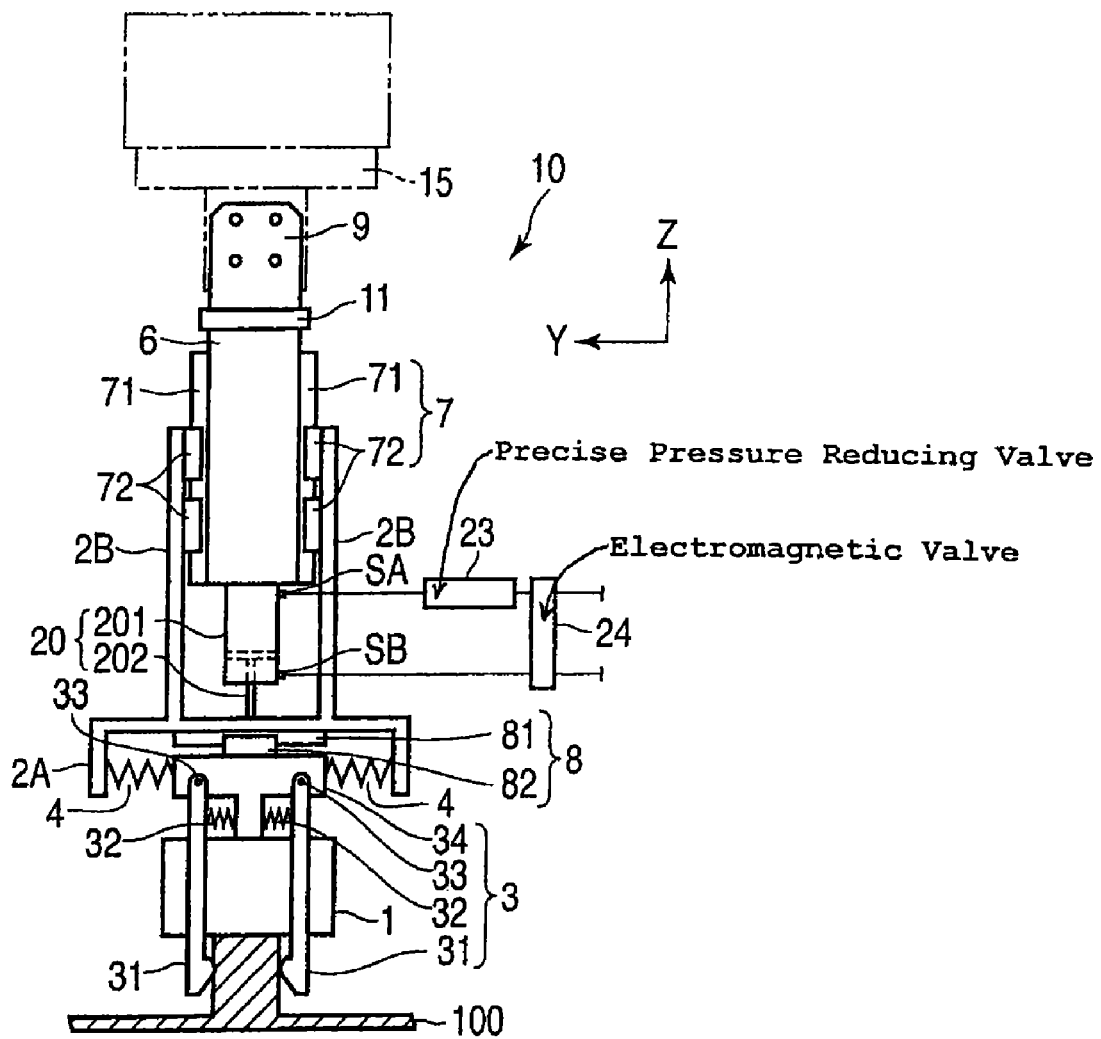
FIG. 1B is a constitutional diagram showing a state where the copying apparatus according to the first embodiment of the present invention grasps the workpiece.
Figure 1C:
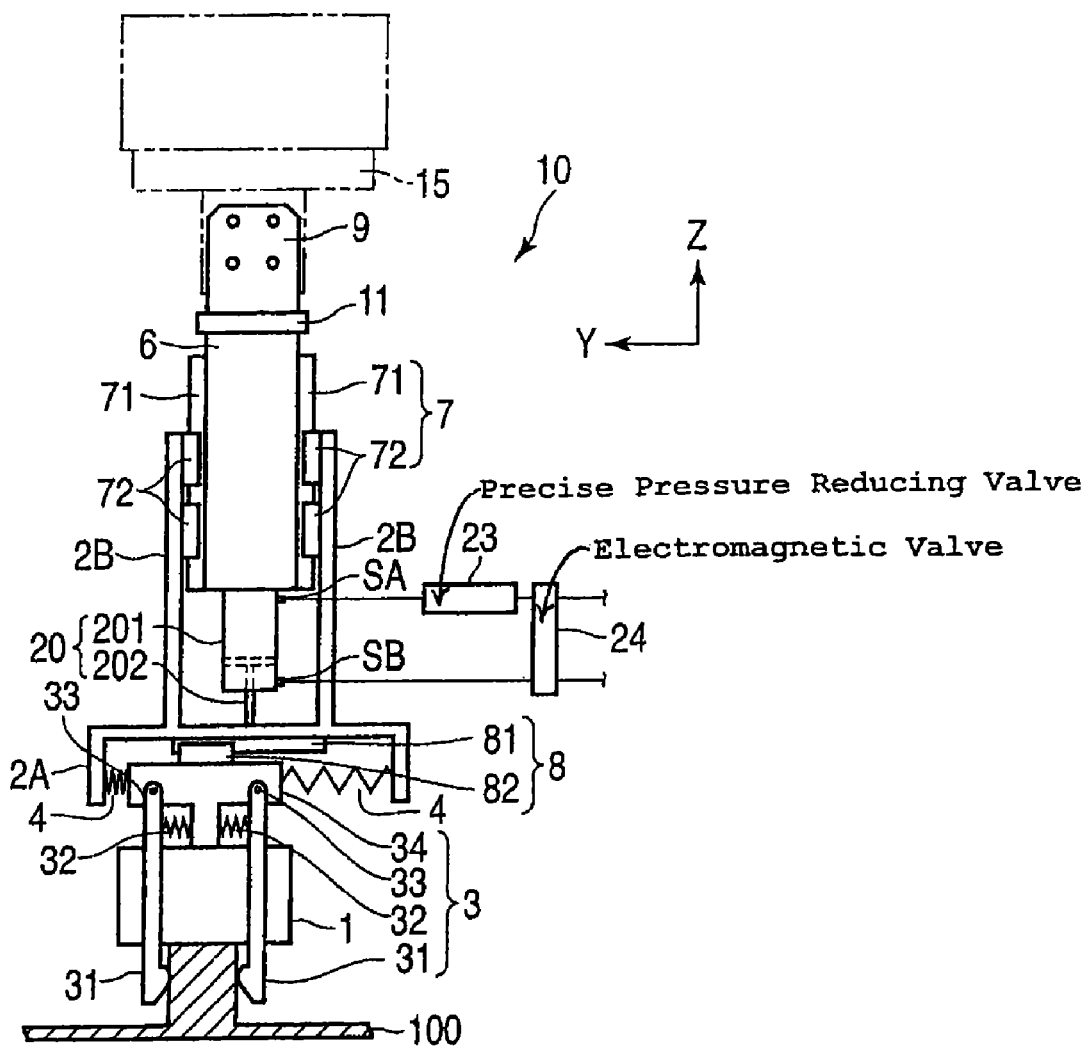
FIG. 1C is a constitutional diagram showing a state where a lateral translatory slide guide of the copying apparatus according to the first embodiment of the present invention moves.

Each of FIGS. 1A, 1B, and 1C is a constitutional diagram showing an operation of a copying apparatus 10 according to a first embodiment of the present invention. Here, an X axis, Y axis, and a Z axis are axes orthogonal to each other. Further, a direction in which a workpiece 100 is copied (a traveling direction of the copying apparatus is a direction (an X axis direction) vertical to a page space of the drawing. It is to be noted that like reference numerals denote like parts to omit a detailed explanation thereof in the following description and a repeated description will be likewise omitted in subsequent embodiments.

The copying apparatus 10 includes a shoe 1, frames 2A and 2B, a clamping mechanism 3, two elastic bodies 4, a slide portion 6, four vertical translatory slide guides 7, a lateral translatory slide guide 8, a fixing portion 9, a connecting plate 11, an air cylinder 20, a precise pressure reducing valve 23, and an electromagnetic valve 24.

The clamping mechanism 3 clamps the workpiece 100 from both sides with respect to a traveling direction. As a result, the copying apparatus 10 copies in a state where the clamping mechanism 3 grasps the workpiece. The clamping mechanism 3 includes two contact shoes 31, a clamping mechanism main body 34, two pins 33 that fasten the two contact shoes 31 on the clamping mechanism main body 34, and two elastic bodies 32 that pull the two contact shoes 31 toward the inner side.

The two contact shoes 31 are fastened on the clamping mechanism main body 34 with the pins 33. The two contact shoes 31 can move with the pins 33 fastening the contact shoes 31 being used as supporting points, respectively. Each of the two contact shoes 31 has a distal end having a tapered shape. As a result, the two contact shoes 31 facilitate grasping the workpiece 100. The two contact shoes 31 are connected with a protrusion through the respective elastic bodies 32 with the protrusion protruding below the clamping mechanism 34 at the center. Therefore, the two contact shoes 31 are pulled toward the inner side by the respective elastic bodies 32. Consequently, the two contact shoes 31 generate a force constantly clamping the workpiece 100 from a contracting force of the two elastic bodies 32.

A shoe 1 is a portion that is brought into contact with the workpiece 100 which is to be copied. The shoe 1 is disposed to the clamping mechanism main body 34.

The lateral translatory slide guide 8 enables relative movement of the clamping mechanism 3 in a lateral direction (a direction orthogonal to a copying direction) with respect to the frame 2A. The lateral translatory slide guide 8 includes a rail 81 and a block 82. The rail 81 is disposed on a lower side of the frame 2A. The block 82 is disposed on an upper side of the clamping mechanism main body 34. With such a structure, the lateral translatory slide guide 8 slides along the rail 81 in the lateral direction with respect to the traveling direction in which the copying apparatus 10 performs copying.

The two elastic bodies 4 are connected with portions between the frame 2A and both sides of a direction in which the lateral slide guide 8 of the clamping mechanism main body 34 laterally moves, respectively. The two elastic bodies 4 perform centering of the clamping mechanism 3 and the shoe 1 by using stretching force thereof.

The frame 2B is fixed to an upper side of the frame 2A. It is to be noted that the frame 2B may be integrally formed with the frame 2A.

The four vertical translatory slide guides 7 are provided to support four corners of the slide portion 6. Specifically, two vertical translatory slide guides 7 are provided on each of both sides of the slide portion 6. The two vertical translatory slide guides 7 disposed on each side of the slide portion 6 are provided to be placed at both ends. The vertical translatory slide guide 7 relatively moves the slide portion 6 in the vertical direction with respect to the frame 2B. The vertical translatory slide guide 7 includes a rail 71 and two blocks 72. The rail 71 is fixed to the slide portion 6. The blocks 72 are fixed to the frame 2B. The two blocks 72 are separately provided on an upper side and a lower side to support the movable slide portion 6 that can move in the vertical direction. This structure enables the slide portion 6 to move up and down along the rail 71.

The air cylinder 20 is provided on the lower side of the slide portion 6. The air cylinder 20 expands and contracts in a direction in which the slide portion 6 can slide (i.e., an up-and-down direction) by the vertical translatory slide guides 7. The air cylinder 20 is a device that controls protrusion/retraction of the shoe 1. That is, when the air cylinder 20 is operated, the frames 2A and 2B, the clamping mechanism 3, and the shoe 1 can be moved in the vertical direction.

As a result, when, e.g., a discontinuous portion of the workpiece 100 is found during copying of the workpiece 100, the shoe 1 can be lifted up by the air cylinder 20 to prevent the shoe 1 from being fitted into the discontinuous portion.

Furthermore, the air cylinder 20 is also an elastic element that buffers a pressing stroke of the copying apparatus 10B. Based on the elastic element of the air cylinder 20, the copying apparatus 10 has a buffering function when the workpiece 100 is pressed. As a result, the copying apparatus 10 does not apply an excessive pressing force. The air cylinder 20 tolerates displacement in the vertical direction when copying the workpiece 100.

The air cylinder 20 includes a cylinder 201 and a rod 202. The cylinder 201 is fixed to the slide portion 6. The rod 202 is fixed to a frame 2C.

The precise pressure reducing valve 23 controls an air pressure in the air cylinder 20. The precise pressure reducing valve 23 is installed to control an air pressure on an SA side (an upper side) of the air cylinder 20. The precise pressure reducing valve 23 has a relief function. The precise pressure reducing valve 23 is arranged in an air pressure circuit between the air cylinder 20 and a compressed air supply source (a primary side). An electromagnetic valve 24 that is driven by a control device which is omitted in the drawing is provided in this air pressure circuit. Moreover, it is assumed that a device such as a filter is also arranged in this air circuit as required.

The fixing portion 9 fixes the copying apparatus 10 to a feeder 15. The fixing portion 9 moves the fixed copying apparatus 10 in each direction by using the feeder 15.

The connecting plate 11 is provided between the fixing portion 9 and the slide portion 6. The connecting plate 11 connects the plurality of copying apparatuses 10. Therefore, when the single copying apparatus 10 alone is used, the connecting plate 11 may be omitted to directly connect the fixing portion 9 to the slide portion 6.

An operation of the copying apparatus 10 will now be described.

FIG. 1A is a constitutional diagram showing a state before the copying apparatus 10 operates. FIG. 1B is a constitutional diagram showing a state where the copying apparatus 10 grasps the workpiece 100. FIG. 1C is a constitutional diagram showing a state where the lateral translatory slide guide 8 of the copying apparatus 8 moves.

The copying apparatus 10 starts from a state where the shoe 1 is lifted above the workpiece 100.

First, the copying apparatus 10 drives the air cylinder 20 to move down the shoe 1 toward the workpiece 100. As a result, in the copying apparatus 10, the contact shoes 31 brought into contact with the workpiece 100 are opened to clamp the workpiece 100 as shown in FIG. 1B. In the copying apparatus 10, a distal end of each contact shoe 31 is formed into a tapered shape to facilitate grasping the workpiece 100, and the elastic bodies 4 are provided to perform centering of the clamp mechanism 3 and the shoe 1. Therefore, the copying apparatus 10 can grasp the workpiece 100 by just pressing the shoe 1 and the clamp mechanism 3 against the workpiece 100 by using the air cylinder 20.

A force constantly acts on the contact shoes 31 in a direction in which the elastic bodies 32 contract. Therefore, a clamping force is constantly applied to the workpiece 100.

The air cylinder 20 applies a pressing force that is used to press the shoe 1 against the workpiece. To generate this pressing force, compressed air is supplied to the SA side through the precise pressure reducing valve 23 having the relief function.

A copying operation of the copying apparatus 10 is performed by actuating the air cylinder 20 with the shoe 1 being appressed against the workpiece 100 as shown in FIG. 1B (in the illustrated example, the copying apparatus 10 is moved in the vertical direction in the page space of the drawing).

Even if displacement is produced in the vertical direction of the copying apparatus 10 and the workpiece 100 due to, e.g., a control error of the feeder 15 or bending of the workpiece 100, the displacement can be absorbed by the air cylinder 20.

Further, it is assumed that the moving direction of the feeder 15 and the workpiece 100 are displaced in the lateral direction. Even in this case, the copying apparatus 10 can slide in the lateral direction by the lateral translatory slide guide 8 with the workpiece 100 being clamped by the clamping mechanism 3 as shown in FIG. 1C. Therefore, the shoe 1 held by the clamping mechanism 3 can slide together with the clamping mechanism 3, and displacement caused due to a control error of the feeder 15 or lack of positional accuracy of the workpiece 100 can be tolerated.

As explained above, the shoe 1 can be protruded/retracted by using the air cylinder 20 as required. Therefore, even if the workpiece 100 has, e.g., a discontinuous portion, copying can be performed while preventing the shoe 1 from being fitted into the discontinuous portion.

This will now be described while taking a copying operation of a copying apparatus 10U constituted by connecting the four copying apparatuses 10 as an example. It is to be noted that a description will be given as to the structure having the four copying apparatuses 10 for the sake of convenience, but any number of the copying apparatuses 10 can be used.

Each of FIGS. 4A, 4B, 4C, and 4D is a constitutional diagram showing a state of a copying apparatus of the copying apparatus 10U according to this embodiment. FIGS. 4A to 4D sequentially show states of the copying operation performed by the copying apparatus 10U. In FIGS. 4A to 4D, copying apparatuses 10a, 10b, 10c, and 10d are equivalent to the copying apparatus 10. Furthermore, portions constituting the copying apparatus 10a have reference numerals denoted in FIGS. 1A to 1C with an auxiliary symbol a. Likewise, portions constituting the copying apparatuses 10b to 10d have suffixes b to d, respectively.

In the copying apparatus 10U, the four copying apparatuses 10 are configured as one unit. In the copying apparatus 10U, a connecting plate 11 of one copying apparatus 10 is extended to be connected with the four copying apparatuses 10. Air pressure circuits of air cylinders 20a to 20d are independent in accordance with each of the copying apparatuses 10a to 10d. The pressure of the compressed air that is supplied to the SA side of each air cylinder 20 imparts a constant pressing force of each shoe 1 based on adjustment using each precise pressure reducing valve 23. As a result, each shoe 1 can constantly obtain an appropriate adhesion force with respect to a workpiece 100A.

The workpiece 100A is a long workpiece with a partially discontinuous portion HL. A jig 14 that fixes the workpiece 100A is provided at an end of the workpiece 100A.

As shown in FIG. 4A, in the copying apparatus 10U, when the copying apparatus 10a reaches the discontinuous portion HL, a non-illustrated control device outputs a signal to actuate an electromagnetic valve 24a. When the electromagnetic valve 24a is actuated, the air cylinder 20 is driven to move up a shoe 1a. In this manner, the copying apparatus 10U controls the shoe 1a to be protruded/retracted before an interference occurs.

Likewise, when the copying apparatus 10b, 10c, or 10d reaches the discontinuous portion HL, an electromagnetic valve 24b, 24c, or 24d is actuated to move up a shoe 1b, 1c, or 1d.

Figure 4C:
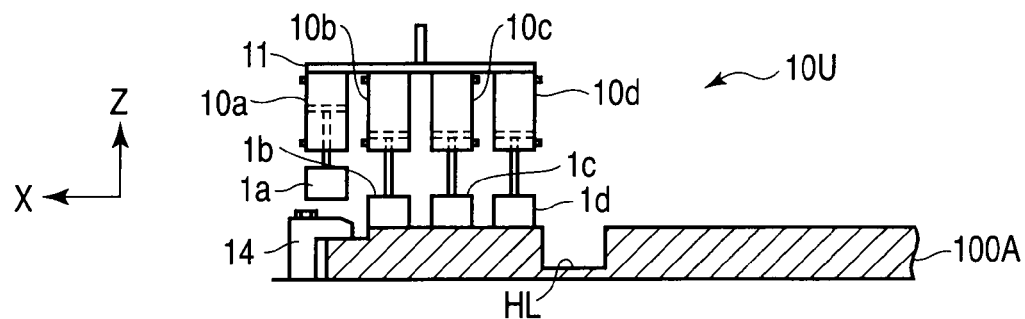
FIG. 4C is a constitutional diagram showing a state of a third stage of the copying operation performed by the copying apparatus according to the first embodiment of the present invention.
Figure 4D:
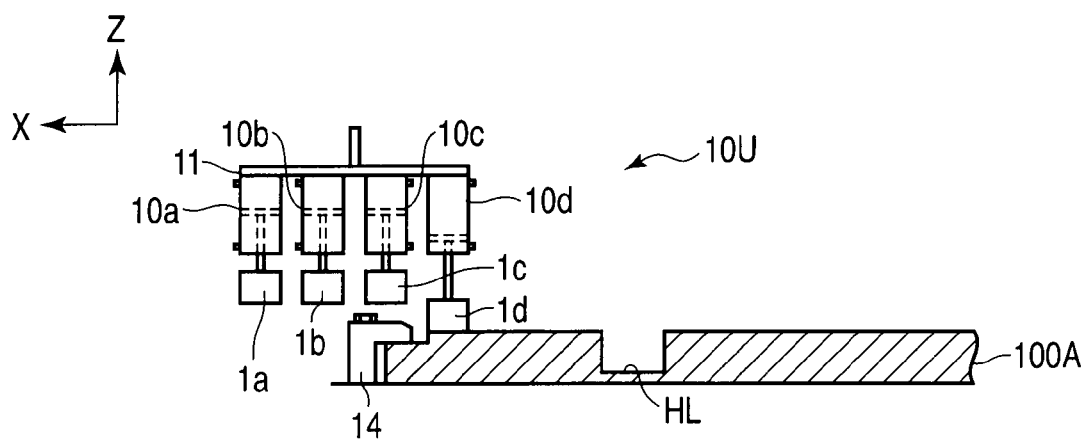
FIG. 4D is a constitutional diagram showing a state of a fourth stage of the copying operation performed by the copying apparatus according to the first embodiment of the present invention.

In the copying apparatus 10U, as shown in FIG. 4C, when the copying apparatus 10a reaches the jig 14, the non-illustrated control device outputs a signal to actuate the electromagnetic valve 24a. When the electromagnetic valve 24a is actuated, the air cylinder 20 is driven to move up the shoe 1a. In this manner, the copying apparatus 10U controls the shoe 1a to be protruded/retracted before an interference occurs.

Likewise, when the copying apparatus 10b, 10c, or 10d reaches the jig 14, the electromagnetic valve 24b, 24c, or 24d is actuated to move up the shoe 1b, 1c, or 1d.

As explained above, when each of the copying apparatuses 10a to 10d reaches a part near an interferer, e.g., the discontinuous portion HL of the workpiece 100A and the jig 14, the copying apparatus 10U performs an operation of moving the shoe 1 in a direction in which interference with each of the shoes 1a to 1d is avoided by using each of the air cylinders 20a to 20d in response to a signal from the control device.

When another workpiece 100A is present in a traveling direction and the copying operation must be continued, the copying apparatus 10U can again press each shoe 1 against the workpiece 100A to restart the copying operation.

According to this embodiment, since the workpiece 100 can be clamped, even if displacement occurs due to control or lack of positional accuracy of the workpiece 100, the copying apparatus 10 can tolerate this displacement to perform copying.

The copying apparatus can avoid an interference with, e.g., a discontinuous portion and copy a necessary region by an operation thereof. Therefore, the copying apparatus 10 can prevent the shoe 1 from being fitted into the discontinuous portion HL of the workpiece 100A or from interfering with the jig 14 that fixes the workpiece 100A during the operation of copying the workpiece 100A.

When the copying apparatus 10U is constituted of the plurality of copying apparatuses 10, it can copy the workpiece by using the plurality of shoes 1a to 1d in a single copying operation.

Second Embodiment

FIG. 5 is a front view showing a structure of a copying apparatus 10A according to a second embodiment of the present invention. Furthermore, a direction in which a workpiece 100 is copied (a traveling direction of the copying apparatus) is determined as a direction vertical to a page space of the drawing (an X axis direction).

The copying apparatus 10A has a structure where both side surfaces of a shoe 1 in the X axis direction are fastened to a clamping mechanism main body 34A by using pins 16A in the copying apparatus 10 according to the first embodiment shown in FIGS. 1A to 1C. To realize such a structure, the clamping mechanism main body 34A is obtained by deforming a shape of the clamping mechanism main body 34 of the copying apparatus 10. Other points are the same as for the copying apparatus 10.

In the copying apparatus 10A, the shoe 1 can be oscillated in a rolling direction by using the pins 16A.

According to this embodiment, in addition of the functions and effects of the first embodiment, copying can be performed while absorbing, e.g., a control error of a feeder 15 or an attachment error of the workpiece 100.

Third Embodiment

Figure 6:
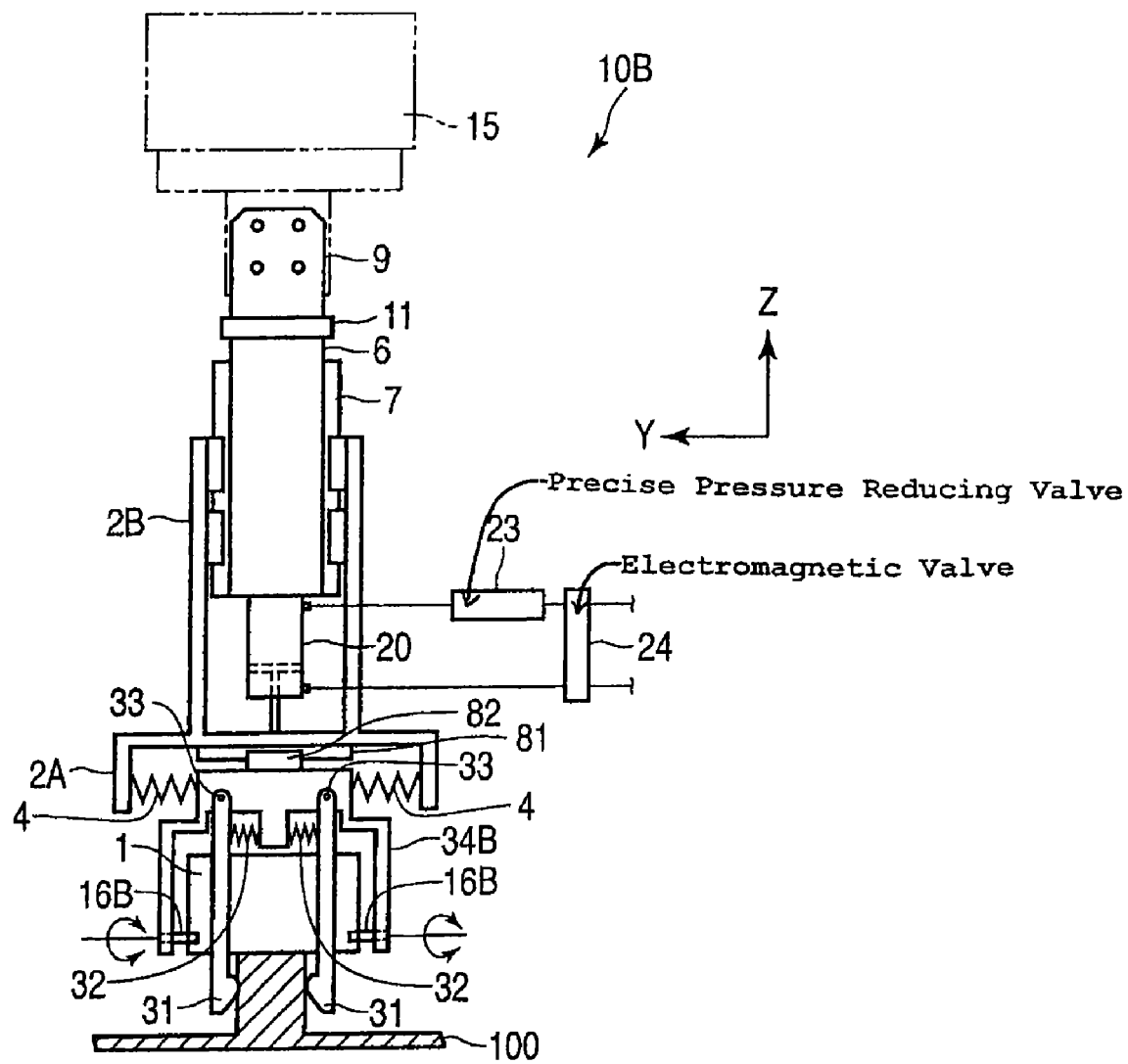
FIG. 6 is a front view showing a structure of a copying apparatus according to a third embodiment of the present invention.

FIG. 6 is a front view showing a structure of a copying apparatus 10B according to a third embodiment of the present invention. Moreover, a direction in which a workpiece 100 is copied (a traveling direction of the copying apparatus) is determined as a direction vertical to a page space of the drawing (an X axis direction).

The copying apparatus 10B has a structure in which both side surfaces of a shoe 1 in a Y axis direction are fastened to a clamping mechanism main body 34B by pins 16B in the copying apparatus 10 according to the first embodiment depicted in FIGS. 1A to 1C. To realize such a structure, the clamping mechanism main body 34B is obtained by modifying a shape of the clamping mechanism main body 34 of the copying apparatus 10. Other points are the same as for the copying apparatus 10.

In the copying apparatus 10B, the shoe 1 can be oscillated in a pitch direction by pins 16B.

According to this embodiment, in addition to the functions and effects of the first embodiment, copying can be performed while absorbing, e.g., a control error of a feeder 15 or an attachment error of the workpiece 100.

Fourth Embodiment

Figure 7:
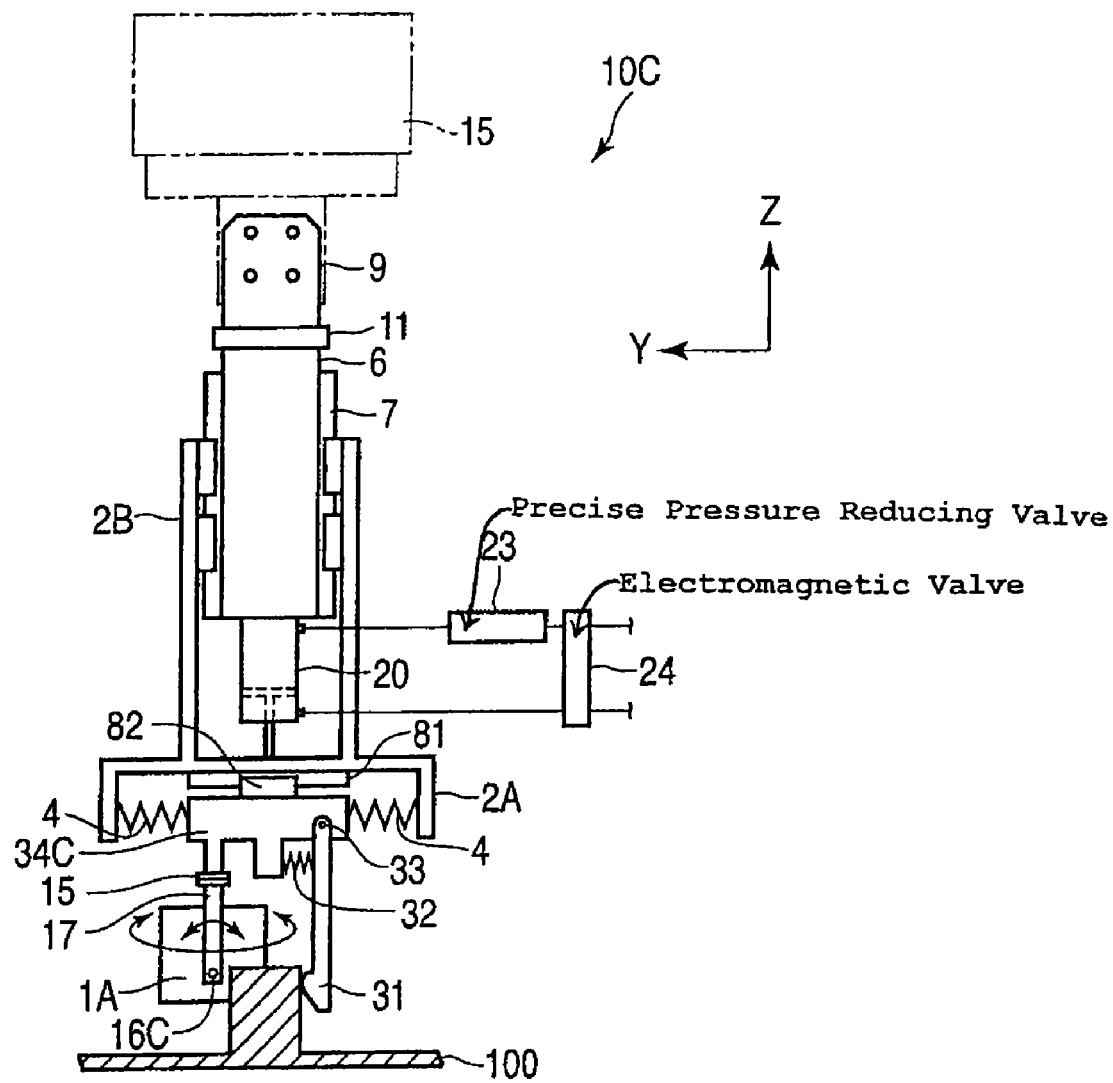
FIG. 7 is a front view showing a structure of a copying apparatus according to a fourth embodiment of the present invention.

FIG. 7 is a front view showing a structure of a copying apparatus 10C according to a fourth embodiment of the present invention. Additionally, a direction in which a workpiece 100 is copied (a traveling direction of the copying apparatus) is determined as a direction vertical to a page space of the drawing (an X axis direction).

The copying apparatus 10C has a structure where both side surfaces of a shoe 1A in an X axis direction are fastened on the a clamping mechanism main body 34C by pins 16C and a bearing 15 is provided between the clamping mechanism main body 34C and the shoe 1A to connect the bearing 15 with the shoe 1A through an arm 17 in the copying apparatus 10 according to the first embodiment depicted in FIGS. 1A to 1C. To realize this structure, the clamping mechanism main body 34C is obtained by modifying a shape of the clamping mechanism main body 34 in the copying apparatus 10. Other points are the same as for the copying apparatus 10.

In the copying apparatus 10C, the shoe 1A can be oscillated in a rolling direction by the pins 16C. Further, the bearing 15 enables rotating the shoe 1A, the pins 16C and the arm 17 holding these members in a yawing direction.

According to this embodiment, in addition to the functions and effects of the first embodiment, copying can be performed while absorbing, e.g., a control error of the feeder 15 or an attachment error of the workpiece 100.

Fifth Embodiment

Figure 8:
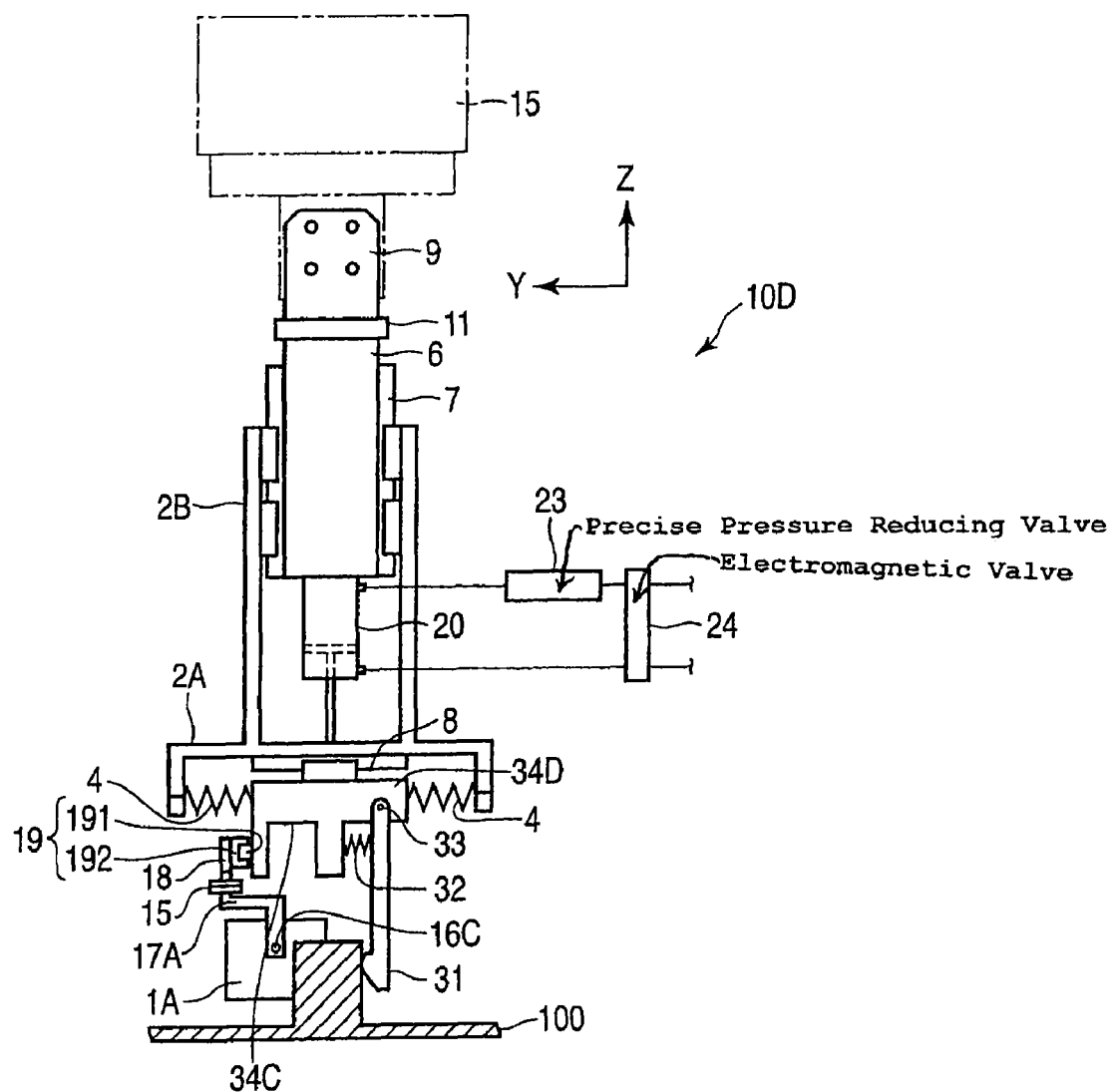
FIG. 8 is a front view showing a structure of a copying apparatus according to a fifth embodiment of the present invention.

FIG. 8 is a front view showing a structure of a copying apparatus 10D according to a fifth embodiment of the present invention. Further, a direction in which a workpiece 100 is copied (a traveling direction of the copying apparatus) is determined as a direction vertical to a page space of the drawing (an X axis direction).

The copying apparatus 10D has a structure in which an arc slide guide 19 disposed to a clamping mechanism main body 34D and a bearing 15 are provided in place of one of the two contact shoes 31, the arc slide guide 19 and the bearing 15 are held by an arm 18, the shoe 1 is substituted by a shoe 1A, and the bearing 15 and the shoe 1A are held by an arm 17 in the copying apparatus 10 according to the first embodiment depicted in FIGS. 1A to 1C. To realize such a structure, the clamping mechanism main body 34D is obtained by modifying a shape of the clamping mechanism main body 34 in the copying apparatus 10. Other points are the same as for the copying apparatus 10.

The arc slide guide 19 is arranged on a side surface of the clamping mechanism 3 and disposed to allow its oscillating movement in a pitch direction as the traveling direction of the copying apparatus 10D. The arc slide guide 19 includes a rail 191 and a block 192. The rail 191 is fixed on a side surface of the clamping mechanism main body 34D. The block 192 is fixed to the arm 18. The block 192 can slide to describe an arc with respect to the rail 191. An axis of rotation of the arc slide guide 19 is provided on a surface where the shoe 1A comes into contact with the workpiece 100.

FIG. 9 is a side view showing a structure realized by two copying apparatuses 10D1 and 10D2 according to this embodiment.

A basic structure of each of the copying apparatuses 10D1 and 10D2 is the copying apparatus 10D.

A shoe 1AA and a shoe 1AB of the copying apparatus 10D1 and the copying apparatus 10D2 have different shapes. Furthermore, the shoe 1AA and the shoe 1AB have different contact positions O1 and O2 at which they come into contact with a workpiece 100, respectively. Therefore, arc slide guides 19A and 19B of the copying apparatus 10D1 and the copying apparatus 10D2 have different turning radii. It is to be noted that the arc slide guides 19A and 19B having the same turning radius may be adopted.

FIG. 10 is a constitutional diagram showing a state where the shoe 1AB of the copying apparatus 10D2 according to this embodiment is inclined.

Since the axis of rotation of the shoe 1AB in the copying apparatus 10D2 is provided on a contact surface of the workpiece 100, positional displacement in the X direction does not occur.

When the two copying apparatuses 10D1 and 10D2 are used to copy the workpiece 100, two different positions on the workpiece 100 can be simultaneously copied in a single copying operation.

According to this embodiment, in addition to the functions and effects of the first embodiment, the arc slide guides 19 can absorb an error generated in a pitch direction or an error of a work disposal position at the time of a copying operation. Furthermore, since a variation in the X direction as the traveling direction of each copying apparatus 10D does not have to be taken into consideration, disposition of a control surface can be simplified.

Therefore, in each copying apparatus 10D, when each arc slide guide 19 is arranged at the portion where the shoe 1A is held, the workpiece can be copied while absorbing an error in the pitch direction as the traveling direction for copying and determining a workpiece surface as the axis of rotation.

Sixth Embodiment

Figure 11A:
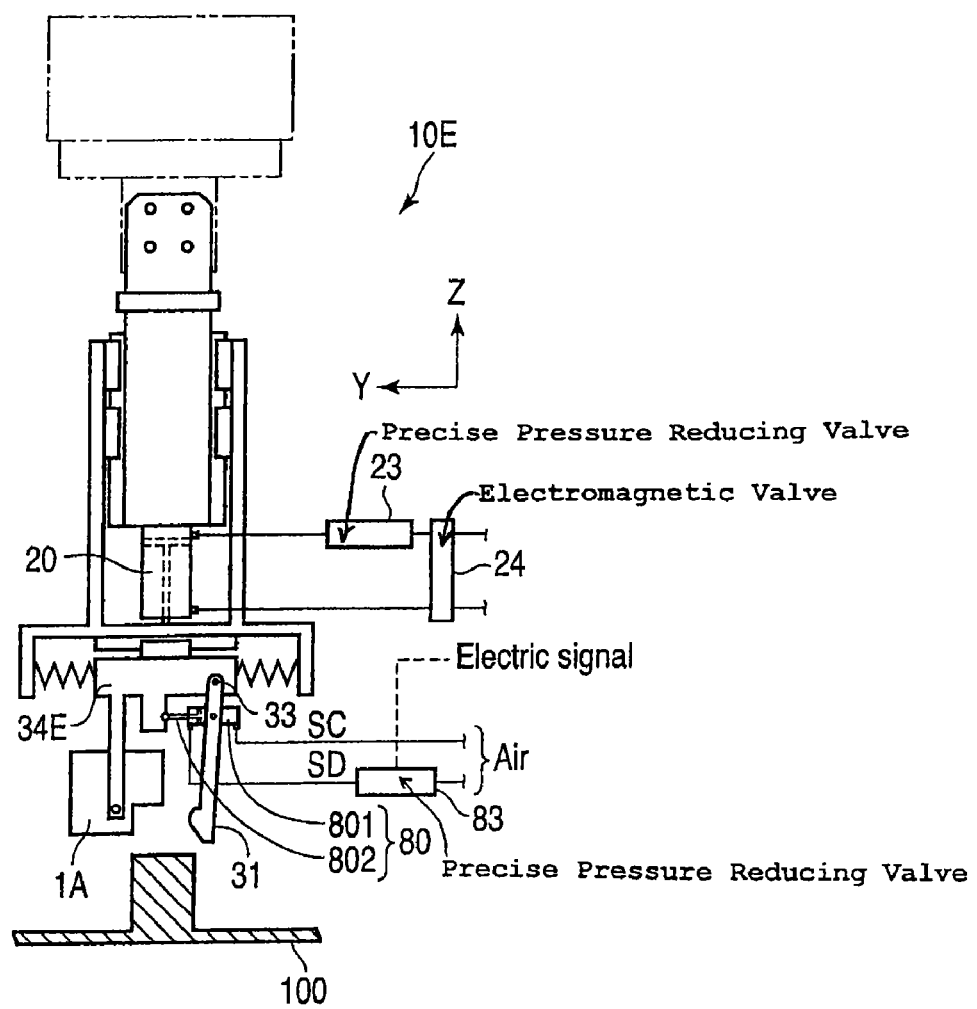
FIG. 11A is a constitutional diagram showing a state before a copying apparatus according to a sixth embodiment of the present invention grasps a workpiece.
Figure 11B:
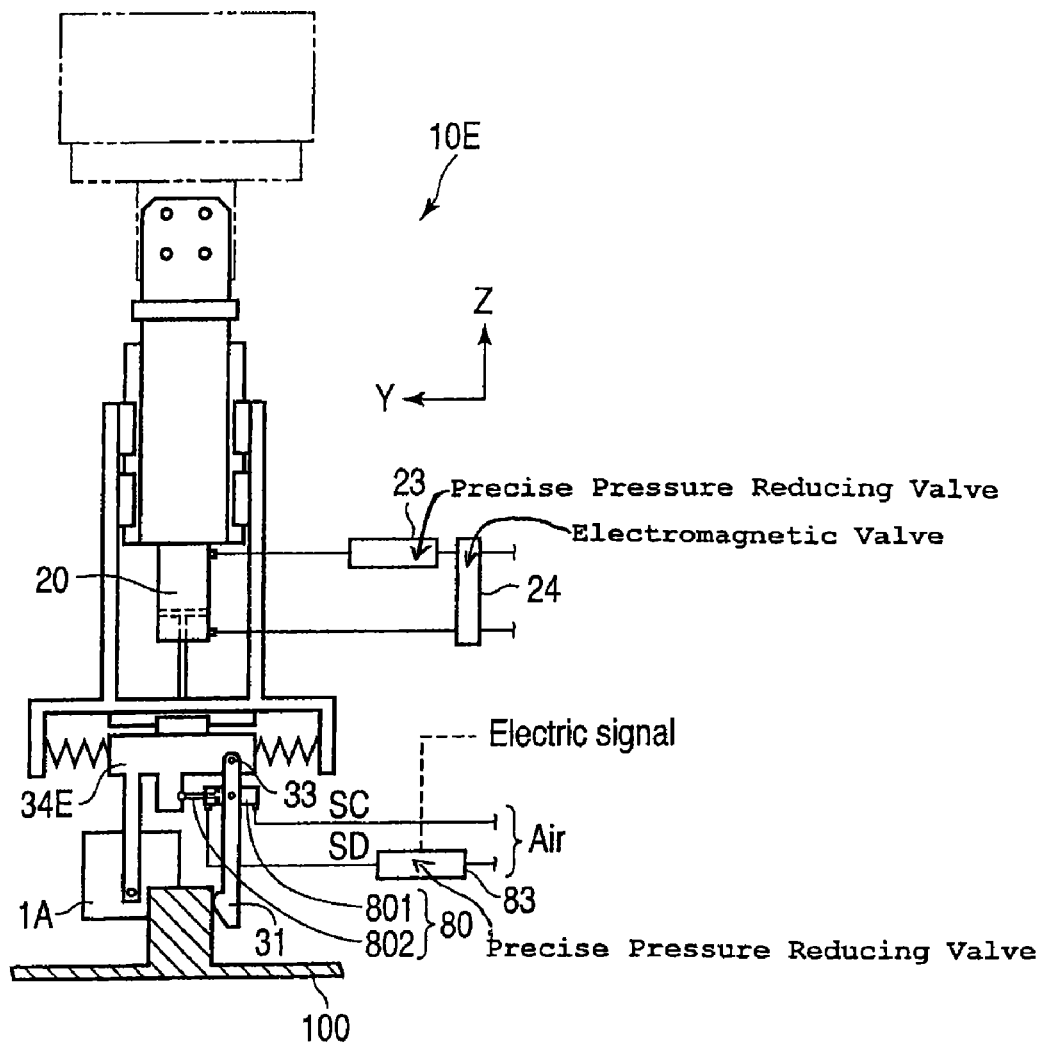
FIG. 11B is a constitutional diagram showing a state where the copying apparatus according to the sixth embodiment of the present invention grasps the workpiece.
Figure 11C:
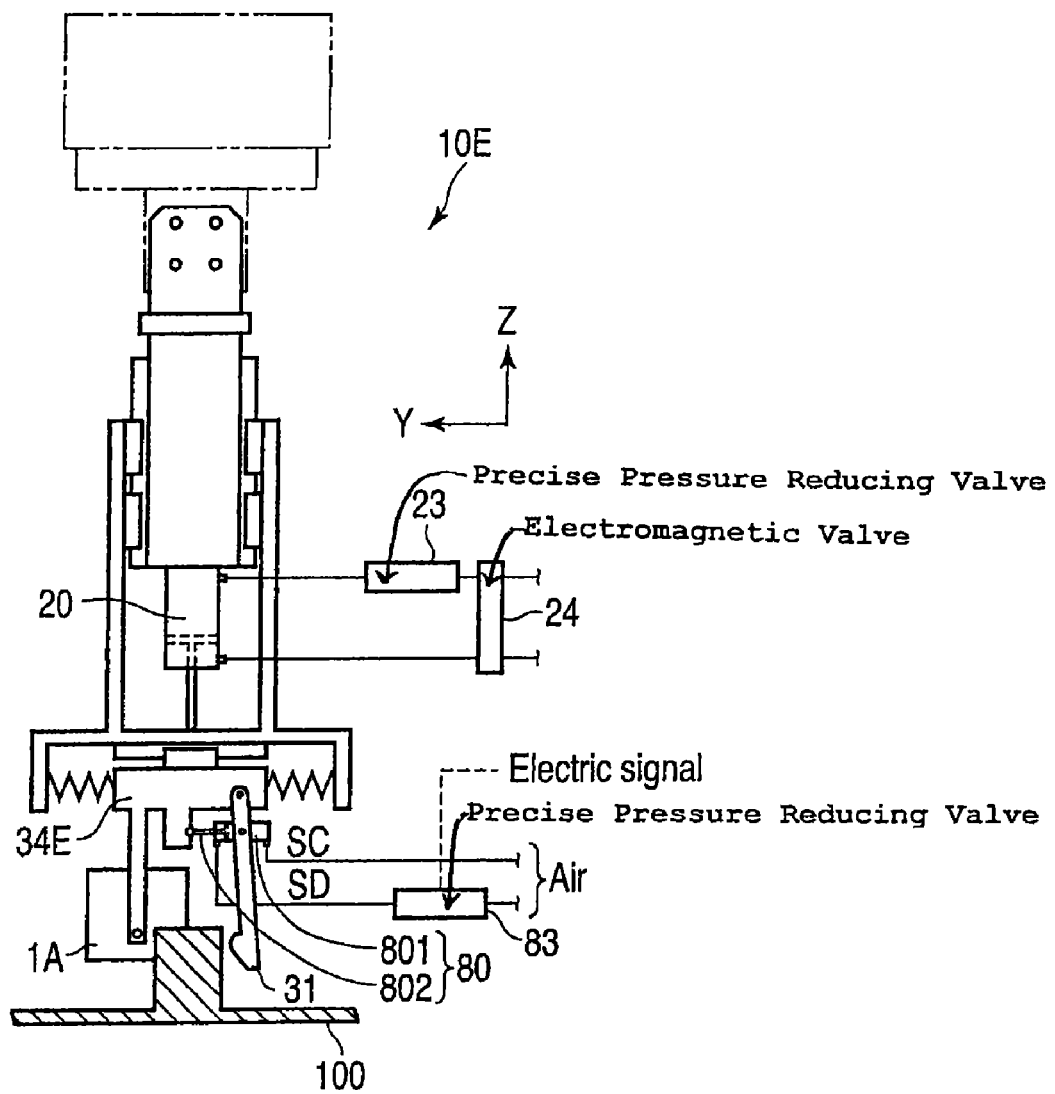
FIG. 11C is a constitutional diagram showing a state where a contact shoe of the copying apparatus according to the sixth embodiment of the present invention is opened.

Each of FIGS. 11A, 11B, and 11C is a constitutional diagram showing an operation of a copying apparatus 10E according to a sixth embodiment of the present invention.

The copying apparatus 10E has a structure where one 31 of the two contact shoes 31 and one elastic body 32 connected with this contact shoe 31 are removed, an air cylinder 80 is provided in place of the other elastic body 32, a shoe 1A is provided in place of the shoe 1, and a clamping mechanism main body 34E is provided in place of the clamping mechanism main body 34 in the copying apparatus 10 according to the first embodiment depicted in FIGS. 1A to 1C. An air pressure circuit including a precise pressure reducing valve 83 is connected with the air cylinder 80. Other points are the same as for the copying apparatus 10.

A side of the clamping mechanism main body 34E where the contact shoe 31 is not provided is extended like an arm to have substantially the same length as the contact shoe 31. The shoe 1A is disposed at a distal end of the arm-like extended portion of the clamping mechanism main body 34E. This clamping mechanism clamps the workpiece 100 by using the contact shoe 31 and the shoe 1A.

The shoe 1A has a shape formed to copy, e.g., a corner portion of the workpiece 100, and the shoe 1A can grasp the workpiece 100 when it faces the contact shoe 31.

The air cylinder 80 generates a force that pulls the contact shoe 31 toward the inner side. As a result, the air cylinder 80 generates a force for grasping (clamping) the workpiece 100. The air cylinder 80 includes a cylinder 801 and a rod 802. The cylinder 801 is disposed to the contact shoe 31 to allow its oscillating movement. The rod 802 is disposed to the clamping mechanism main body 34 to allow its oscillating movement.

The precise pressure reducing valve 83 controls the air pressure in the air cylinder 80. That is, the precise pressure reducing valve 83 supplies compressed air to the air cylinder 80. The precise pressure reducing valve 83 has a relief function. The precise pressure reducing valve 83 is arranged in an air pressure circuit between the air cylinder 80 and a compressed air supply source (a primary side). The precise pressure reducing valve 83 can adjust the pressure of the air that is fed to the air cylinder 80 in response to an electric signal output from a non-illustrated control device. A device such as an electromagnetic valve or a filter is also arranged in this air circuit as required.

An operation of grasping (clamping) the workpiece 100 by the copying apparatus 10E will now be described.

FIG. 11A is a constitutional diagram showing a state before the copying apparatus 10E grasps the workpiece 100. FIG. 11B is a constitutional diagram showing a state where the copying apparatus 10E grasps the workpiece 100. FIG. 11C is a constitutional diagram showing a state where the contact shoe 31 of the copying apparatus 10E is opened.

The contact shoe 31 grasps the workpiece 100 by applying a pressure to the SD side in such a manner that the air cylinder 80 contracts. The contact shoe 31 releases the workpiece 100 by applying a pressure to the SC side in such a manner that the air cylinder 80 is expanded.

As the method of clamping the workpiece 100 from the state before the workpiece 100 is grasped shown in FIG. 11A, the copying apparatus 10E operates as follows.

As one method, the copying apparatus 10E actuates an air cylinder 20 to press the shoe 1A against the workpiece 100. As a result, the contact shoe 31 is opened, and the copying apparatus 10E can grasp the workpiece 100.

As another method, the copying apparatus 10E supplies compressed air to the air cylinder 80 in a direction in which the contact shoe 31 is opened (the side) as shown in FIG. 11C. Subsequently, the copying apparatus 10E carries out an operation of bringing the shoe 1A into contact with the workpiece 100 by using the air cylinder 20. Then, the copying apparatus 10E supplies compressed air to the air cylinder 80 in a direction in which the contact shoe 31 is closed (the SD side). As a result, the copying apparatus 10E grasps the workpiece 100. In this case, since the contact shoe 31 is opened from the beginning, the copying apparatus 10E can readily grasp the workpiece 100. Furthermore, the copying apparatus 10E can increase the clamping force after grasping the workpiece 100.

An operation of copying the workpiece 100 by the copying apparatus 10E will now be described.

When using the copying apparatus 10E in an inclined state, the clamping force of the clamping mechanism 3 may be increased or decreased due to the weight of the clamping mechanism 3 itself. Likewise, the pressing force of the shoe 1A may be increased or decreased due to the weight of the shoe 1A itself.

In such a case, the copying apparatus 10E adjusts the force for clamping the workpiece 100 by using the air cylinder 80 and the precise pressure reducing valve 83. In this manner, the copying apparatus 10E reduces an influence of gravitational force and constantly applies an appropriate clamping force. Specifically, the control device outputs an electric signal to the precise pressure reducing valve 83 in accordance with a degree of inclination and changes an air pressure of the precise pressure reducing valve 83 that should be adjusted. Compressed air subjected to pressure adjustment by the precise pressure reducing valve is supplied to the air cylinder 80. In this manner, the clamping force can be controlled in an appropriate pressure range.

The control device can cope with an arbitrary inclination angle by obtaining a clamping force that varies in accordance with an inclination of the copying apparatus 10E and an air pressure required to correct this clamping force in advance.

According to this embodiment, in addition to the functions and effects of the first embodiment, the following functions and effects can be obtained.

The copying apparatus 10E has a structure that is suitable when the apparatus is used in an inclined state. For example, even if the copying apparatus 10E is used in an inclined state, using the precise pressure reducing valve that can adjust an air pressure enables correcting an influence of gravity and constantly applying an appropriate clamping force to the workpiece. Further, even if displacement occurs due to control or lack of positional accuracy of the workpiece, the copying apparatus 10 can tolerate this displacement and perform copying.

Furthermore, the copying apparatus 10E has a structure that is also suitable when a width dimension of the workpiece varies. For example, when an elastic body is used for clamping, a position of the contact shoe varies depending on a width of the workpiece, and hence the clamping force also varies. However, when the air cylinder is used, fixing an air pressure enables making force for actuating the air cylinder constant. Therefore, a fixed clamping force can be maintained irrespective of a width of the workpiece or a position of the contact shoe.

Seventh Embodiment

Figure 12B:
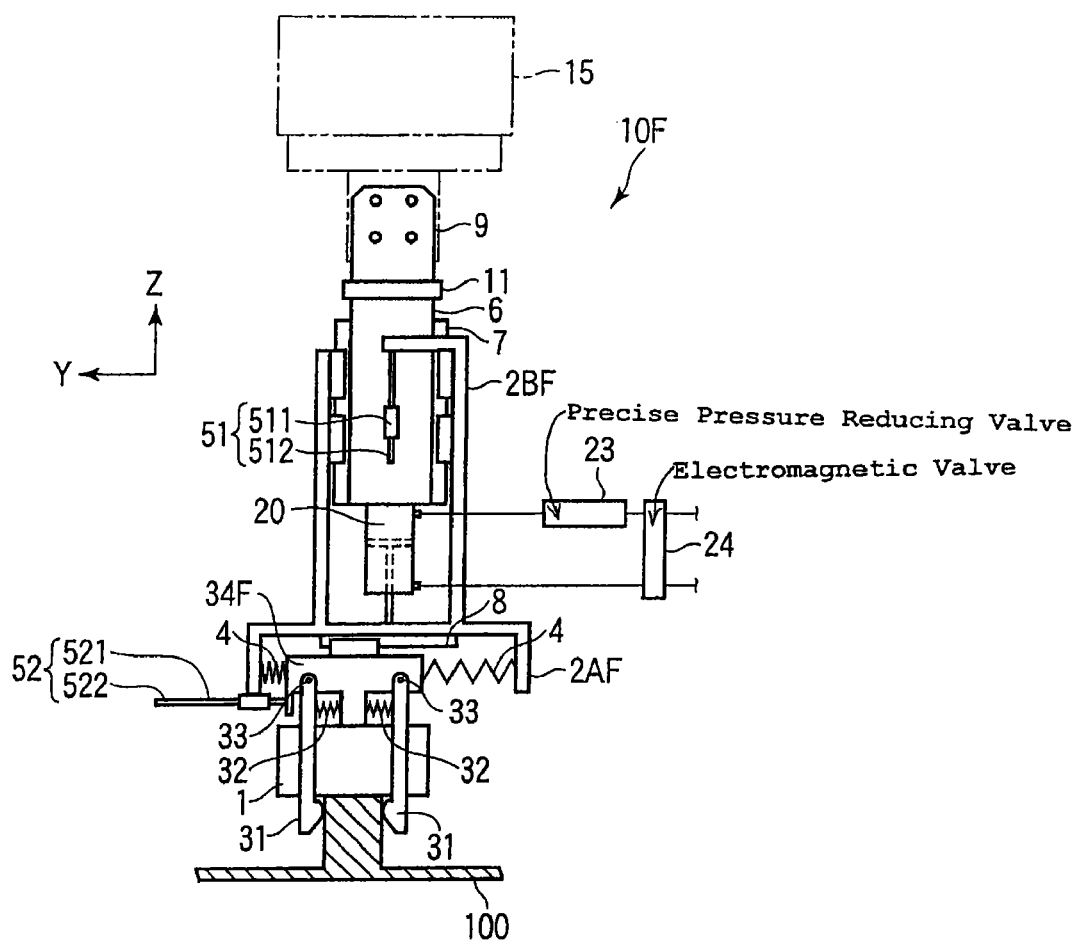
FIG. 12B is a front view showing a structure in a state deviating from an appropriate copying range of the copying apparatus according to a seventh embodiment of the present invention.

Each of FIGS. 12A and 12B is a front view showing a structure of a copying apparatus 10F according to a seventh embodiment of the present invention.

The copying apparatus 10F has a structure where displacement sensors 51 and 52 are provided in the copying apparatus 10 according to the first embodiment depicted in FIGS. 1A to 1C. Furthermore, to provide the displacement sensors 51 and 52, shapes of the frames 2A and 2B and the clamping mechanism main body 34 are changed to frames 2AF and 2BF and a clamping mechanism main body 34F. Other points are the same as for the copying apparatus 10.

Each of the displacement sensors 51 and 52 is a sensor that detects displacement of a workpiece 100 and a feeder 15 through movement of a shoe 1 that is in contact with the workpiece 100. The displacement sensor 51 or 52 is, e.g., a differential transformer type displacement sensor.

The displacement sensor 51 includes a differential transformer unit 511 and a movable core 512. The differential transformer unit 511 is fixed to a slide portion 6. The movable core 512 is fixed to the frame 2BF. A non-illustrated control device detects relative movement (displacement) of the differential transformer unit 511 and the movable core 512. The control device supplies a signal that is used to move the feeder 15 based on a detection result obtained from this displacement sensor 51.

The differential sensor 52 includes a differential transformer unit 521 and a movable core 522. The differential transformer unit 521 is fixed to a slide portion 2BF. The movable core 522 is fixed to the clamping mechanism main body 34F. The non-illustrated control device detects relative movement (displacement) of the differential transformer unit 521 and the movable core 522. The control device supplies a signal that is used to move the feeder 15 based on a detection result obtained from this displacement sensor 52.

A control method for the copying apparatus 10F carried out by the control device will now be described.

FIG. 12A shows an appropriate copying state of the copying apparatus 10F. FIG. 12B shows a state deviating from the appropriate copying state of the copying apparatus 10F.

The control device detects that the copying apparatus 10F deviates in a vertical direction (a Z axis direction) from an appropriate copying range in a state of the copying apparatus 10F depicted in FIG. 12B by the displacement sensor 51. The control device determines that the copying apparatus 10F deviates in the vertical direction (the Z axis direction) from the appropriate copying range when relative displacement of the movable core 511 and the differential transformer unit 512 in the displacement sensor 51 exceeds a predetermined width. That is, the control device judges how much the workpiece 100 deviates in the vertical direction from a position serving as a reference that is used to determine the appropriate copying range based on a width displacement of the movable core 511 and the differential transfer unit 512.

Therefore, the control device outputs a signal that is used to move the feeder 15 in the vertical direction to fall within the appropriate copying range.

Furthermore, the control device detects that the copying apparatus 10F deviates in a horizontal direction (a Y axis direction) from the appropriate copying range in the state of the copying apparatus 10F depicted in FIG. 12B by using the displacement sensor 52. The control device determines that the copying apparatus 10F deviates in the horizontal direction (the Y axis direction) from the appropriate copying range when relative displacement of the movable core 521 and the differential transformer unit 522 in the displacement sensor 52 exceeds a predetermined width. That is, the control device judges how much the workpiece 100 deviates in the horizontal direction from a position serving as a reference that is used to determine the appropriate copying range based on a width displacement of the movable core 521 and the differential transfer unit 522.

Therefore, the control device outputs a signal that is used to move the feeder 15 in the horizontal direction to fall within the appropriate copying range.

In this manner, the control device restores the feeder 15 to the state shown in FIG. 12A from the state depicted in FIG. 12B. As a result, the copying apparatus 10 is corrected to the state in the appropriate copying range.

According to this embodiment, in addition to the functions and effects of the first embodiment, the following functions and effects can be obtained.

The copying apparatus 10F can detect deformation of the workpiece or control deviation of the feeder 15 during copying of the workpiece by providing the displacement sensors 51 and 52. Therefore, the control device can correct a position of the copying apparatus 10F based on detection results from the displacement sensors 51 and 52. As a result, the copying apparatus 10F can maintain an appropriate copying range to effect copying.

For example, the copying apparatus 10F is suitable for a workpiece whose deformation amount may be possibly large with respect to an expected shape of the workpiece. Even if a shape of the workpiece is slightly different from a shape of the workpiece expected before copying, the copying apparatus 10F can constantly maintain the workpiece in the appropriate copying range by moving the feeder 15 that holds the copying apparatus 10F in accordance with detection results from the displacement sensors 51 and 52.

Therefore, when the copying apparatus 10F can grasp the workpiece, even if a shape of the workpiece is slightly different from an intended shape of the workpiece, the copying apparatus 10F can tolerate this difference in shape and copy the workpiece.

Eighth Embodiment

FIG. 13 is a side view showing a structure of a copying apparatus 10UA according to an eighth embodiment of the present invention.

In the copying apparatus 10UA, a sensor 30 that detects a workpiece end portion or an interferer is provided to the copying apparatus 10U according to the first embodiment depicted in FIGS. 1A to 1C on a traveling direction side for copying. Other points are the same as for the copying apparatus 10U.

In the copying apparatus 10UA, it is assumed that intervals between shoe 1a and shoe 1b, between shoe 1b and shoe 1c, and between shoe 1c and shoe 1d are pitches p1, p2, and p3, respectively.

The sensor 30 is fixed to shoe 1a on the traveling direction side. For example, the sensor 30 is, e.g., a non-contact type sensor. The sensor 30 is a laser type sensor that outputs a laser beam LA to detect an end portion of a workpiece 100A or an interferer. When a measurement target object is not present in a set distance range, the sensor 30 generates a signal. Moreover, when a large measurement target object exceeding the set range is present, the sensor 30 generates a signal. That is, the sensor 30 detects absence of a workpiece or presence of an extraneous material, and generates a signal. Absence of the workpiece corresponds to, e.g., a discontinuous portion or an end portion. The extraneous material is an interferer such as a jig that fixes the workpiece. A non-illustrated control device judges a detection result of the sensor 30.

Next, a copying operation for the workpiece 100A performed by the copying apparatus 10UA will now be explained. A basic operation of the copying apparatus 10UA is the same as that of the copying apparatus 10U described in the first embodiment.

Figure 14B:
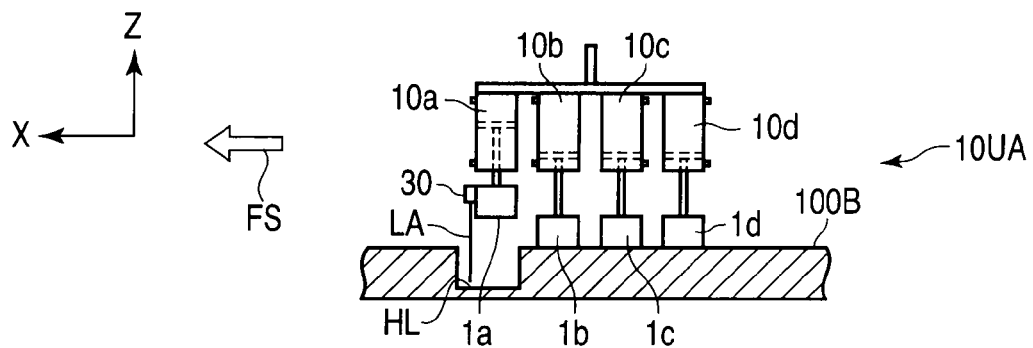
FIG. 14B is a constitutional diagram showing a state of a second stage of the copying operation performed by the copying apparatus according to the eighth embodiment of the present invention.
Figure 14C:
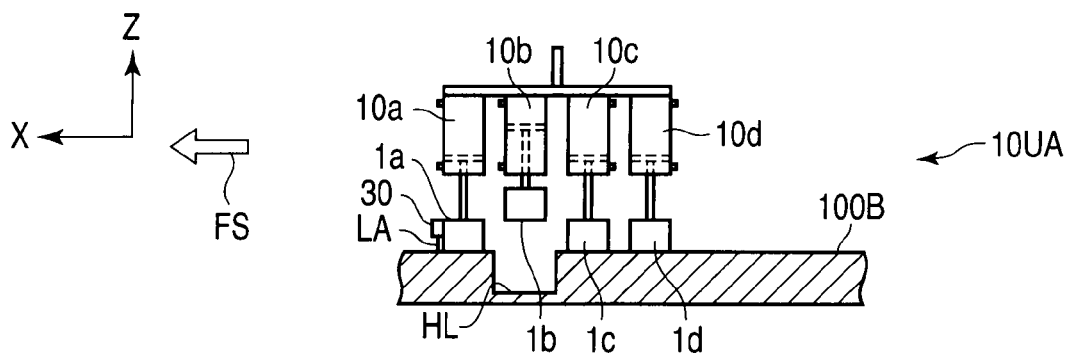
FIG. 14C is a constitutional diagram showing a state of a third stage of the copying operation performed by the copying apparatus according to the eighth embodiment of the present invention.

Each of FIGS. 14A, 14B, and 14C is a constitutional diagram showing an operation of the copying apparatus 10UA according to this embodiment. FIGS. 14A to 14C sequentially show states of the copying operation performed by the copying apparatus 10UA.

A workpiece 100B is a long work piece having a discontinuous portion HL at a part thereof.

The copying apparatus 10UA detects the discontinuous portion HL of the workpiece 100B by using the sensor 30. A signal generated from the sensor 30 upon detection is received by the control device.

When the control device determines that the shoe 1a of the copying apparatus 10UA has reached a position for retraction based on the signal received from the sensor 30, the control device controls an air cylinder 20 of the copying apparatus 10a to move up the shoe 1a.

Here, information indicating that the respective intervals between the shoes 1a to 1d are the pitches p1, p2, and p3 is input to the control device.

After moving the shoe 1a from the discontinuous portion HL, the control device sequentially moves the shoes 1b to 1d every time each shoe advances by each pitch p1, p2, or p3.

In this manner, the shoe 1a can be prevented from falling into the discontinuous portion HL of the workpiece 100B to interfere.

Although the description has been given as to the workpiece B having a discontinuous portion HL at a part thereof, the shoe can likewise avoid an interferer even if this interferer is a different object. For example, the copying apparatus 10UA can likewise avoid the jig 14 of the workpiece 100 described in the first embodiment.

According to this embodiment, in addition to the functions and effects of the first embodiment, the following functions and effects can be obtained.

The copying apparatus 10UA can move the shoes 1a to 1d from the interferer during the copying operation by detecting the interferer by the sensor 30 without programming an operating position of a driving device that protrudes/retracts the shoes 1a to 1d with respect to the target workpiece in advance. Therefore, the copying apparatus 10UA can avoid interference with the workpiece or the jig even during the copying operation.

Ninth Embodiment

Each of FIGS. 15A, 15B, 15C, and 15D is a constitutional diagram showing an operation of a copying apparatus 10UB according to a ninth embodiment of the present invention.

In the copying apparatus 10UB, ultrasonic flaw detectors 90a to 90d are incorporated in the shoes 1a to 1d in the copying apparatus 10U according to the first embodiment depicted in FIGS. 4A to 4D. Therefore, the copying apparatus 10UB is an ultrasonic flaw detection apparatus using the copying apparatus 10U as a copying mechanism. Furthermore, it is assumed that a transmitting medium such as water for ultrasonic flaw detection is supplied separately through, e.g., a hose. Other points are the same as for the copying apparatus 10U.

The ultrasonic flaw detectors 90a to 90d are disposed to detect flaws at different portions of a workpiece to be copied. However, they may be disposed in such a manner that two or more of the ultrasonic flaw detectors 90a to 90d detect flaws at the same portion of the workpiece.

A workpiece 100C as a target of ultrasonic flaw detection is a long workpiece having a discontinuous portion HL at a part thereof. A jig 14 that fixes the workpiece 100C is provided at an end of the workpiece 100C.

An ultrasonic flaw detecting operation (a copying operation) for the workpiece 100C performed by the copying apparatus 10UB will now be described. A basic operation of the copying apparatus 10UB is the same as that of the copying apparatus 10U described in the first embodiment.

FIGS. 15A to 15D sequentially show states of the ultrasonic flaw detecting operation effected by the copying apparatus 10UB.

The workpiece 100C is a long workpiece having the discontinuous portion at a part thereof.

A feeder 15 moves shoes 1a to 1d to a range where flaw detection is required even in the case of detecting flaws of the discontinuous workpiece 100C.

Here, the copying apparatus 10UB can protrude/retract the shoes 1a to 1d by using air cylinders 20 of copying apparatuses 10a to 10d.

Therefore, the copying apparatus 10UB moves away the shoe 1 when the shoe 1 interferes with, e.g., the discontinuous portion of the workpiece 100C or the jig 14.

In this manner, the copying apparatus 10UB performs ultrasonic flaw detection with respect to the long workpiece 100C having the discontinuous portion HL at a part thereof.

According to this embodiment, in addition to the functions and effects of the first embodiment, the following functions and effects can be obtained.

The copying apparatus 10UB can perform ultrasonic flaw detection without interfering with the discontinuous portion HL of the workpiece 100C or the jig 14.

Further, when the ultrasonic flaw detectors 90a to 90d attached to the respective copying apparatuses 10a to 10d constituting the copying apparatus 10UB are disposed to detect flaws at different portions on the workpiece 100C, a plurality of portions of the workpiece 100C can be simultaneously scanned for flaws by the single flaw detecting operation.

10th Embodiment

An ultrasonic flaw detection method for a workpiece 100D performed by the copying apparatus 10UB according to a 10th embodiment will now be described with reference to FIGS. 16A to 27. It is to be noted that a basic structure of the copying apparatus 10UB according to this embodiment is the same as that of the copying apparatus 10UB according to the ninth embodiment. A description will be given as to the copying apparatus 10UB having a structure including two copying apparatuses 10.

This ultrasonic flaw detection method is a method of control by using a feeder 15 and a control device that controls the feeder 15, for example. Furthermore, the copying apparatus 10UB itself or the control device that directly controls the copying apparatus 10UB may include the method of control that carries out a procedure in this method. That is, all of the control leading to an operation of the copying apparatus 10UB carries out this method.

A workpiece 100D as a target of ultrasonic flaw detection is a cylindrical or a tapered workpiece having a circular cross section. The circular cross section does not have to be a perfect circle. The circular cross section may be a cross section having a circular shape, an elliptic shape, or a shape obtained by distorting these shapes. That is, the cross section of the workpiece may be a ring shaped or an arc shape. It is assumed that at least one protrusion 120 is present on an inner side of an outer wall of the workpiece 100D. This protrusion is extended in a longitudinal direction of the workpiece 100D. This protrusion 120 is a direct target of ultrasonic flaw detection.

The method of performing ultrasonic flaw detection with respect to the protrusion 120 by using the copying apparatus 10UB will now be described.

Figure 16A:
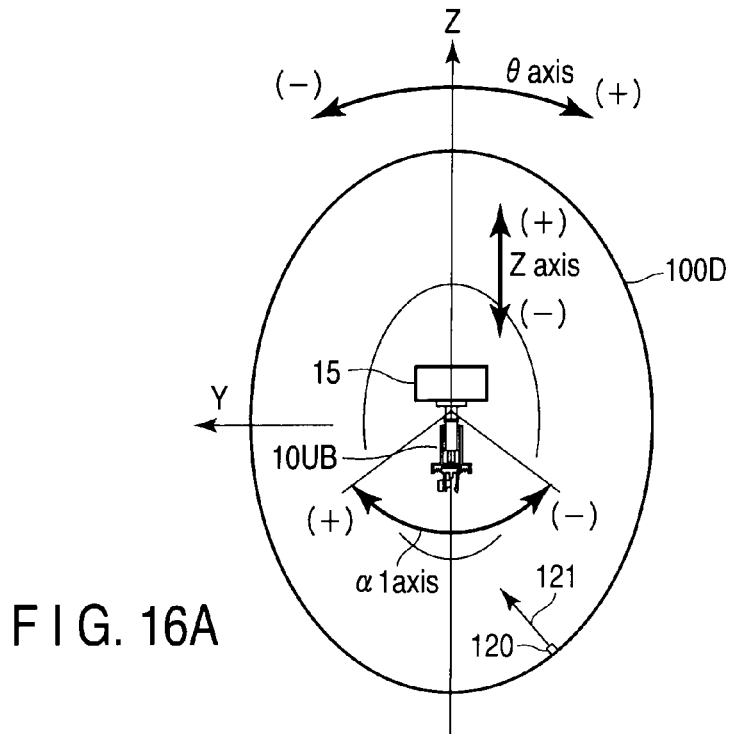
FIG. 16A is a cross-sectional view of a Y-Z plane of a workpiece showing arrangement of a copying apparatus in an ultrasonic flaw detection method according to a 10th embodiment of the present invention.
Figure 16B:
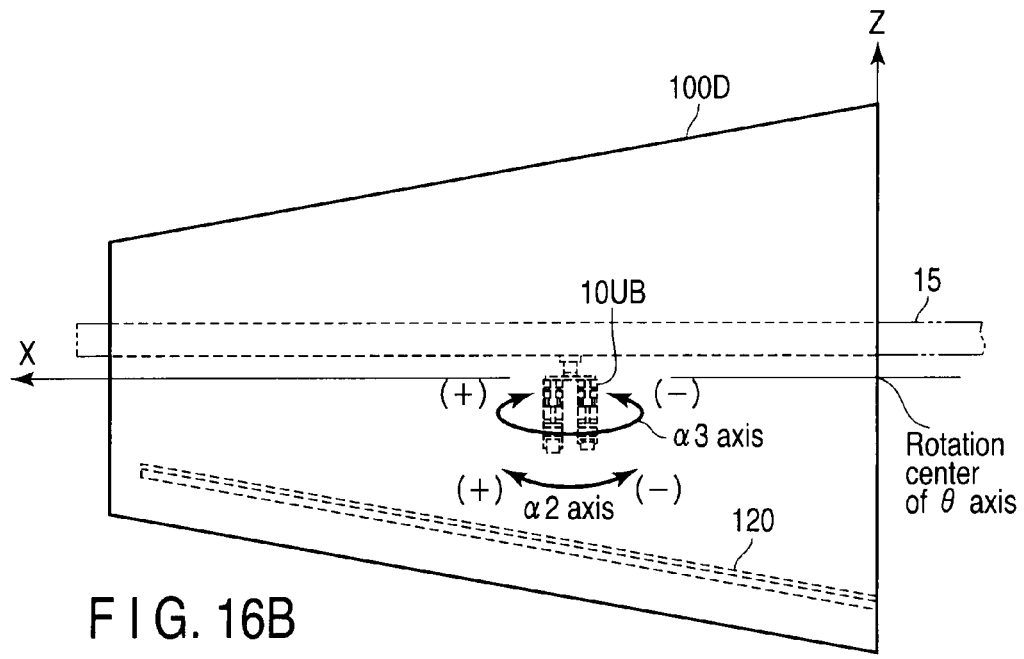
FIG. 16B is a cross-sectional view of a Z-X plane of the workpiece showing the arrangement of the copying apparatus in the ultrasonic flaw detection method according to the 10th embodiment of the present invention.

Each of FIGS. 16A and 16B is a layout drawing showing an arrangement of the copying apparatus 10UB in the ultrasonic flaw detection method according to the 10th embodiment of the present invention. FIG. 16A is a cross-sectional view of a Y-Z plane of the workpiece 100D showing the arrangement of the copying apparatus 10UB in the ultrasonic flaw detection method according to this embodiment. FIG. 16B is a cross-sectional view of a Z-X plane of the workpiece 100D showing the arrangement of the copying apparatus 10UB in the ultrasonic flaw detection method according to this embodiment.

A coordinate system and axes along which the copying apparatus 10UB move will be first described.

A Z axis is a major axis direction of a shape similar to an ellipse as the cross section of the workpiece 100D. The copying apparatus 10UB moves on the Z axis.

A Y axis is a minor axis direction of the shape similar to the ellipse as the cross section of the workpiece 100D. In this ultrasonic flaw detection method, the copying apparatus 10UB is not moved in the Y axis direction. This is because, when the copying apparatus is moved in the Y direction as the minor axis side of the workpiece 100D, the workpiece 100D and the feeder 15 may possibly interfere with each other. An operation (a later-described A axis) of an air cylinder 20 provided in the copying apparatus 10UB compensates for the absence of movement in the Y axis direction. If the major axis and the minor axis of the workpiece 100D are counterchanged in the following example, fixing the Z axis and moving the Y axis can suffice.

An X axis is a longitudinal direction of the workpiece 100D. Further, it is an ultrasonic flaw detecting direction of the copying apparatus 10UB.

A θ axis is a rotation axis of the workpiece 100D.

An α1 axis is a rotation axis of the copying apparatus 10UB around an axis parallel to the rotation axis (the θ axis) of the workpiece 100D.

An A axis is a protruding/retracting direction of the air cylinder 20.

Figure 17:
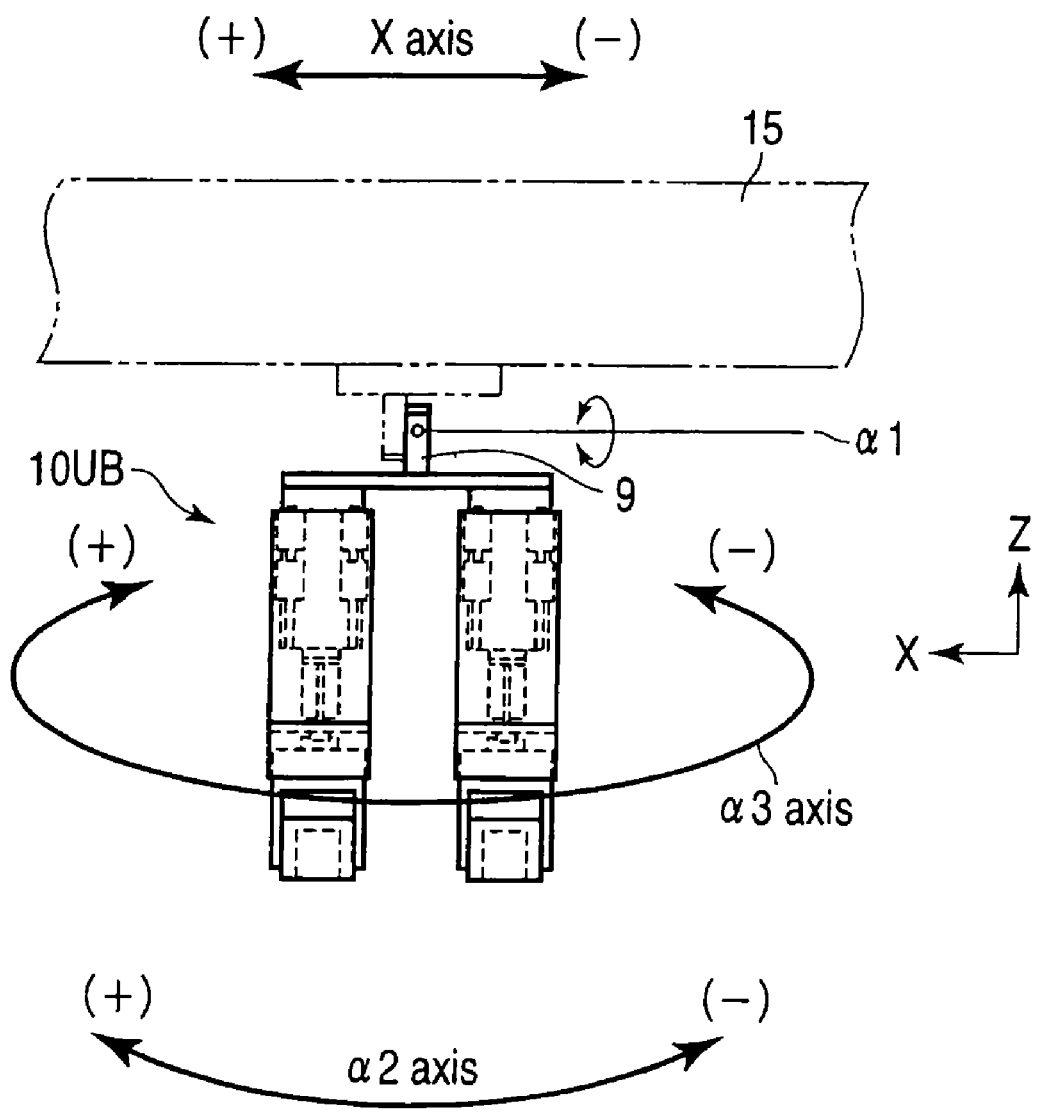
FIG. 17 is a coordinate diagram showing movement of the copying apparatus on a Z-X plane coordinate in the ultrasonic flaw detection method according to the 10th embodiment of the present invention.
Figure 18:
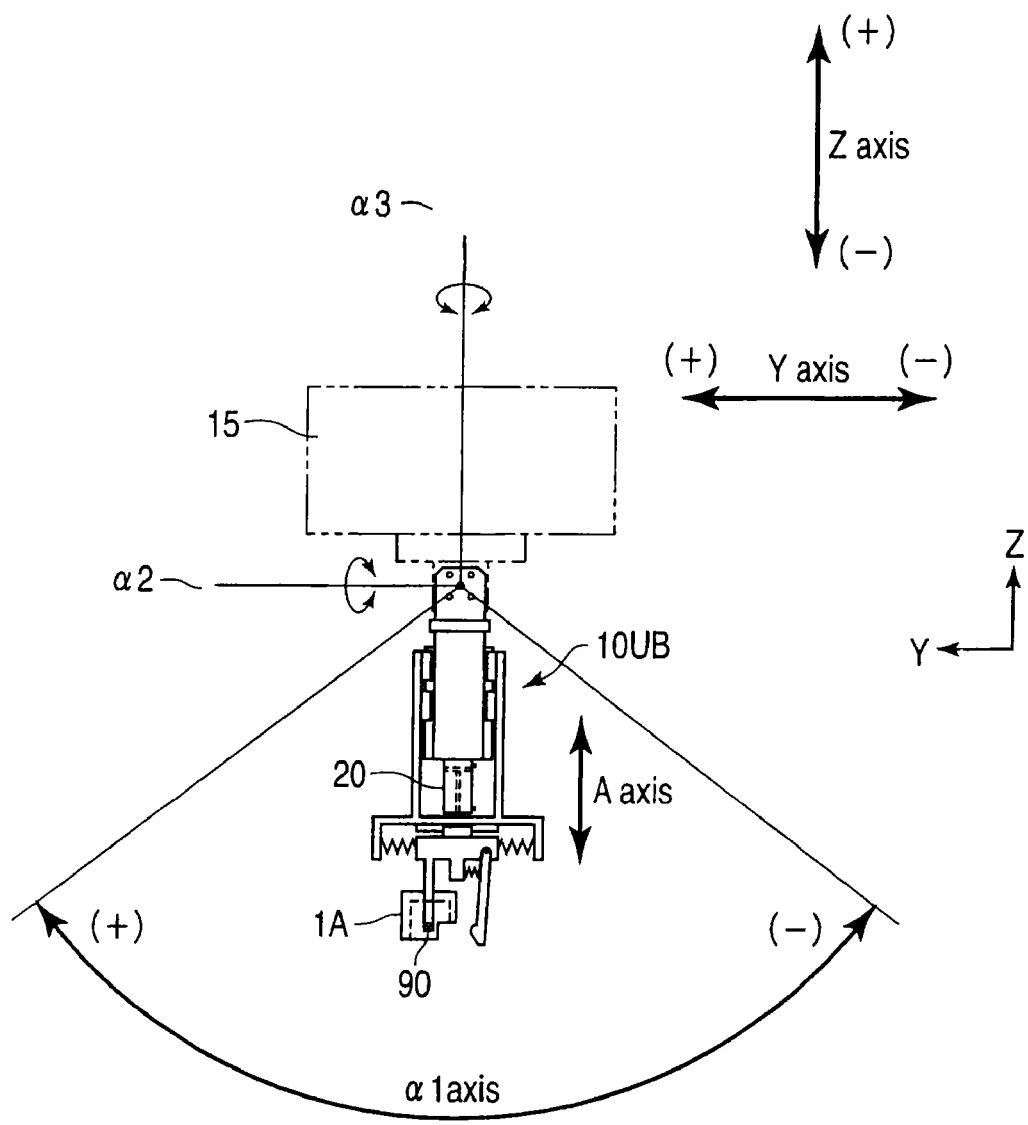
FIG. 18 is a coordinate diagram showing movement of the copying apparatus on a Y-Z plane coordinate in the ultrasonic flaw detection method according to the 10th embodiment of the present invention.

FIG. 17 is a coordinate diagram showing movement of the copying apparatus 10UB on a Z-X plane coordinate in the ultrasonic flaw detection method according to this embodiment. FIG. 18 is a coordinate diagram showing movement of the copying apparatus 10UB on a Y-Z plane coordinate in the ultrasonic flaw detection method according to this embodiment.

An α2 axis is a rotation axis on which the copying apparatus 10UB is rotated to laterally oscillate on the Z-X plane coordinate.

An α3 axis is a rotation axis on which the copying apparatus 10UB is rotated with the A axis direction at the center as shown in FIGS. 17 and 18.

As an outline of this ultrasonic flaw detection method, an inclination angle of the copying apparatus 10UB is first matched with a normal line direction of the protrusion 120, and then ultrasonic flaw detection is carried out in the longitudinal direction (the X direction) of the protrusion 120.

A procedure of matching the inclination angle of the copying apparatus 10UB with the normal line direction of the protrusion 120 will now be described. This procedure is a procedure that is used to provide a state of the copying apparatus 10UB in a posture of ultrasonic flaw detection depicted in FIG. 25.

Figure 25:
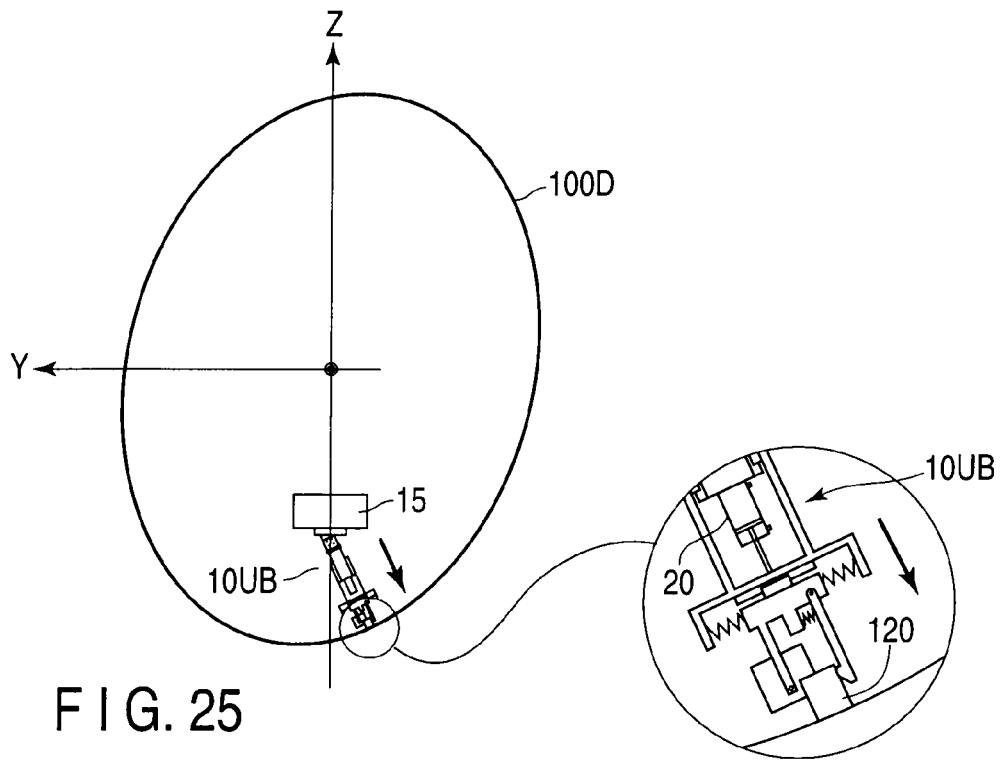
FIG. 25 is a constitutional diagram showing a state of the copying apparatus for explaining a procedure 6 in the ultrasonic flaw detection method according to the 10th embodiment of the present invention.

FIG. 25 is a constitutional diagram showing a state of the copying apparatus 10UB in a posture of ultrasonic flaw detection based on the ultrasonic flaw detection method according to this embodiment. This state is a state where the shoe 1 having the ultrasonic flaw detector 90 embedded therein is appressed against the protrusion 120. Moreover, it is also a state where the inclination angle of the copying apparatus 10UB matches with the near-normal direction of the protrusion 120.

Figure 20:
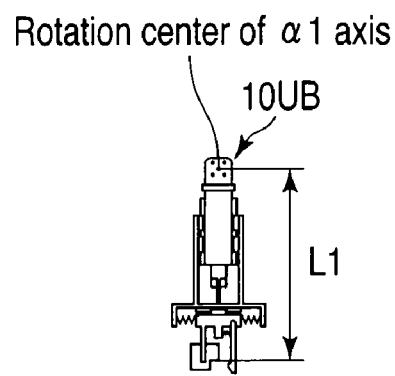
FIG. 20 is a structural view showing a length L1 of the copying apparatus in the ultrasonic flaw detection method according to the 10th embodiment of the present invention.

A length L1 will now be described with reference to FIG. 20.

The length L1 is a length that is most suitable for the copying apparatus 10UB to defect flaws. That is, the length L1 is a length of appropriate contraction of the air cylinder 20 while being appressed against the workpiece 100D. Specifically, the L1 is a length extending from a starting point, which is the rotation center of the α1 axis of the copying apparatus 10UB, to a plane where the shoe 1 is in contact with the workpiece 100D in parallel to the A axis.

Figure 19:
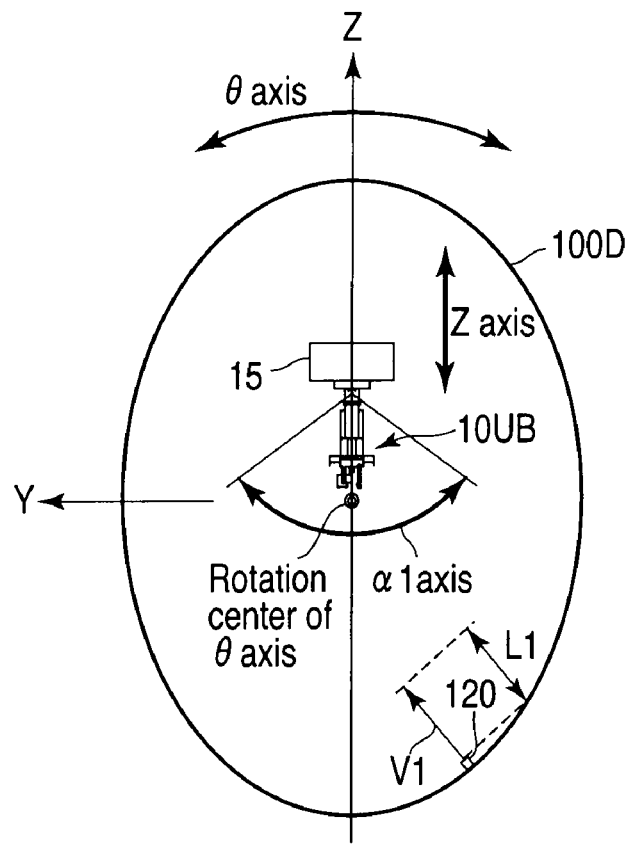
FIG. 19 is a coordinate diagram showing an initial state of the copying apparatus in the ultrasonic flaw detection method according to the 10th embodiment of the present invention.

It is to assumed that the copying apparatus 10UB is in a state depicted in FIG. 19 as an initial state.

As a procedure 1, an angle θ1 formed between a line connecting a distal end point of a normal vector V1 using the protrusion 120 as a starting point with the rotation center of the θ axis and the Z axis is obtained (see FIG. 21). Here, a length of the normal vector V1 of the protrusion 120 is the length L1.

Figure 22:
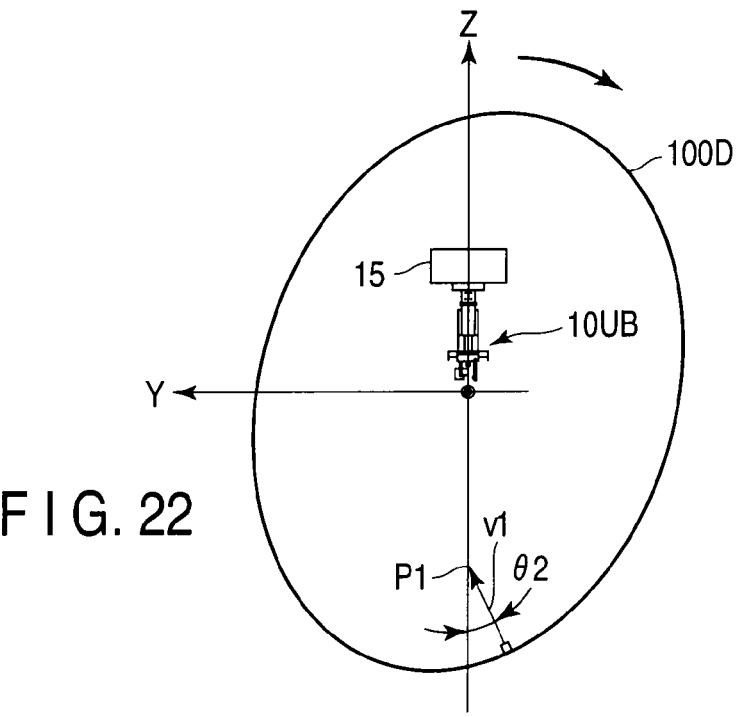
FIG. 22 is a constitutional diagram showing a state of the copying apparatus for explaining a procedure 2 in the ultrasonic flaw detection method according to the 10th embodiment of the present invention.

As a procedure 2, the rotation axis θ on which the workpiece 100D is rotated is turned at an angle θ1 (see FIG. 22). At this time, consideration of the Y-Z plane alone can suffice. Assuming that a coordinate of an ending point of the normal vector V1 is (x, y, z), a rotation amount θ1 is as follows.

$$\theta 1 = \tan^{-1}(y/z)$$

Based on this rotation, the ending point of the normal vector V1 coincides with the Z axis. This point is determined as P1.

As a procedure 3, an angle θ2 formed between the normal vector V1 and the Z axis is obtained (see FIG. 22).

Figure 23:
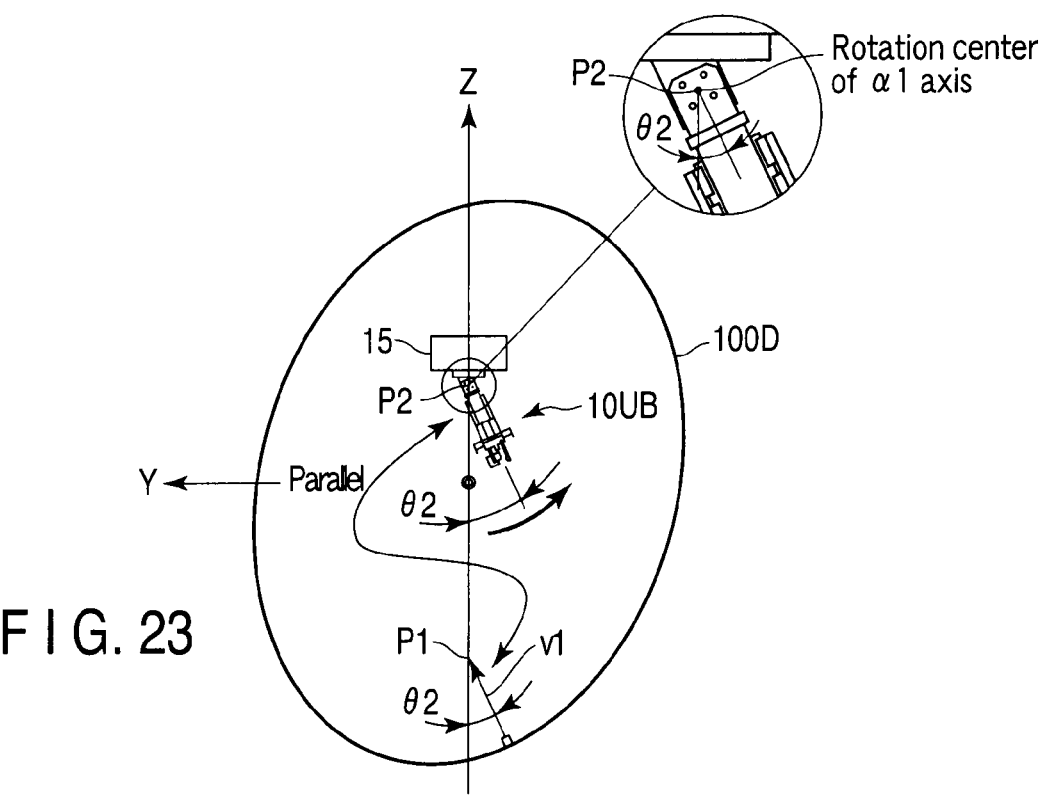
FIG. 23 is a constitutional diagram showing a state of the copying apparatus for explaining a procedure 3 and a procedure 4 in the ultrasonic flaw detection method according to the 10th embodiment of the present invention.

As a procedure 4, the copying apparatus 10UB is turned by an angle θ2 (see FIG. 23). Based on this procedure, the normal vector V1 becomes parallel to the copying apparatus 10UB.

Figure 24:
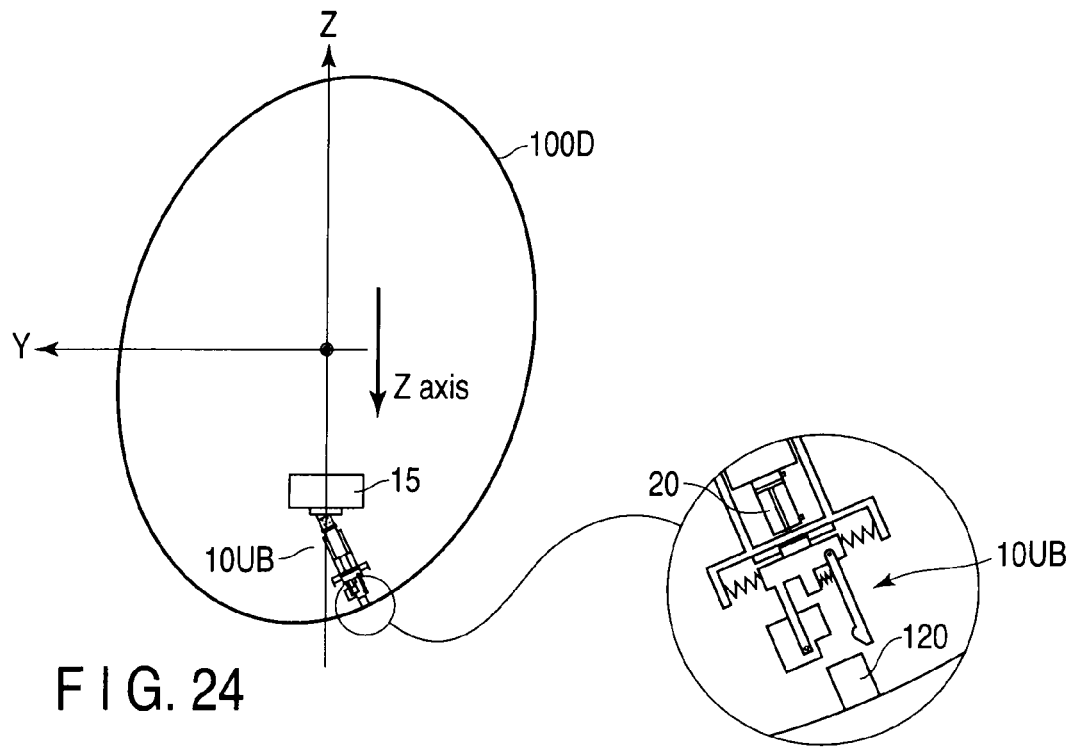
FIG. 24 is a constitutional diagram showing a state of the copying apparatus for explaining a procedure 5 in the ultrasonic flaw detection method according to the 10th embodiment of the present invention.

As a procedure 5, the Z axis of the feeder is moved down in such a manner that a point P2 as the center of the α1 axis of the copying apparatus 10UB coincides with the point P1 determined based on the procedure 2 (see FIG. 24). In this state, a gap is still present between the copying apparatus 10UB and the protrusion 120.

As a procedure 6, the air cylinder 20 of the copying apparatus 10UB is actuated to extend the shoe 1 of the copying apparatus 10UB (see FIG. 25).

Controlling the procedure 1 to the procedure 6 in this manner enables pressing the shoe 1 against the protrusion 120 of the workpiece 100D. The length L1 of copying apparatus 10UB in this state is realized by appropriate contraction of the air cylinder 20.

The reason why the shoe 1 is protruded will now be described. If movement in the Y direction is possible, the normal line can be matched based on an operation of combining the Z direction and the Y axis (an oblique operation). However, as explained above, movement in the Y direction is impossible. Instead, this oblique operation can be carried out by protrusion/retraction of the shoe 1 of the copying apparatus 10UB.

As shown in FIG. 25, after the normal line is matched, the feeder 15 is moved in the X axis direction (the longitudinal direction) of the protrusion 120 to perform ultrasonic flaw detection.

When moving the feeder 15 in the X axis direction, a normal line direction of the protrusion 120 may constantly vary depending on a shape (e.g., a tapered shape) of the workpiece 100D. In this case, the operations of the procedures 1 to 5 must be constantly carried out with movement in the X direction.

Additionally, when the workpiece 100D has, e.g., a tapered shape, axial rotation on such two axes is as shown in FIG. 26, i.e., an α2 axis and an α3 axis. In regard to this rotation direction, as shown in FIGS. 17 and 18, vectors must be formed by using coordinates of two points in a traveling direction and a posture of the copying apparatus must be changed around the two axes, for example.

Further, when a change in stroke in the Z direction is large and the copying apparatus 10UB does not reach the protrusion 120, a posture of the feeder 15 in the X axis direction is inclined as shown in FIG. 27 to cope with this situation, for example.

Furthermore, when the copying apparatus 10UB is inverted 180 degrees on the α3 axis to move the feeder 15, a lower number of the ultrasonic flaw detectors than the number of planes as flaw detection targets can be used to detect flaws on planes of the protrusion 120.

According to this embodiment, the following functions and effects can be obtained.

According to this embodiment, when the functions of the copying apparatus 10UB are used, ultrasonic flaw detection of the protrusion 120 provided on the inner surface of the workpiece 100D can be carried out while avoiding interference with the workpiece 100D or absorbing an error due to, e.g., control of the feeder 15. Therefore, ultrasonic flaw detection exploiting the functions of the copying apparatus 10UB can be effected.

This ultrasonic flaw detection method is suitable for ultrasonic flaw detection for a longeron provided on, e.g., an inner surface of an airframe of an aircraft. That is, the longeron is regarded as the protrusion 120 on the inner surface of the workpiece when this method is applied. As a result, moving the ultrasonic flaw detector 90 along the longeron enables performing ultrasonic flaw detection.

Even if a space of an inner surface of, e.g., a front portion or a rear portion of a streamlined airframe is narrow, applying this method as explained above enables performing flaw detection while avoiding interference between the feeder 15 and the workpiece 100D. Furthermore, even if the longeron is discontinuous, protruding/retracting the shoe 1 enables avoiding interference with the discontinuous portion. Likewise, ultrasonic flaw detection can be carried out while absorbing a rotation error of a non-illustrated rotating device or an installation error of the workpiece.

It is to be noted that each embodiment can be modified and carried out as follows.

In each embodiment, attachment of the rail 71 and the blocks 72 of the vertical translatory slide guides 7 may be opposite to that in the above-described structure. That is, the copying apparatus may have a structure in which the rail 71 is fixed to the frame 2B and the blocks 72 are fixed to the slide portion 71. Likewise, structures of the rail 81 and the block 82 of the lateral translatory slide guide 8 may be opposite. Moreover, the number or the disposal direction of the vertical translatory slide guides 7 or the lateral translatory slide guide 8 are not restricted as long as the functions can be obtained.

In the copying apparatus according to each embodiment, the elastic body 4 may be eliminated. For example, under conditions where clamping is facilitated, e.g., a size, a shape, or a centering range of a workpiece is small, a structure where the elastic body 4 is omitted can be adopted.

In each embodiment, the number of contact shoes, which is two in each foregoing embodiment, is arbitrary as long as a clamping force is generated.

Figure 2:
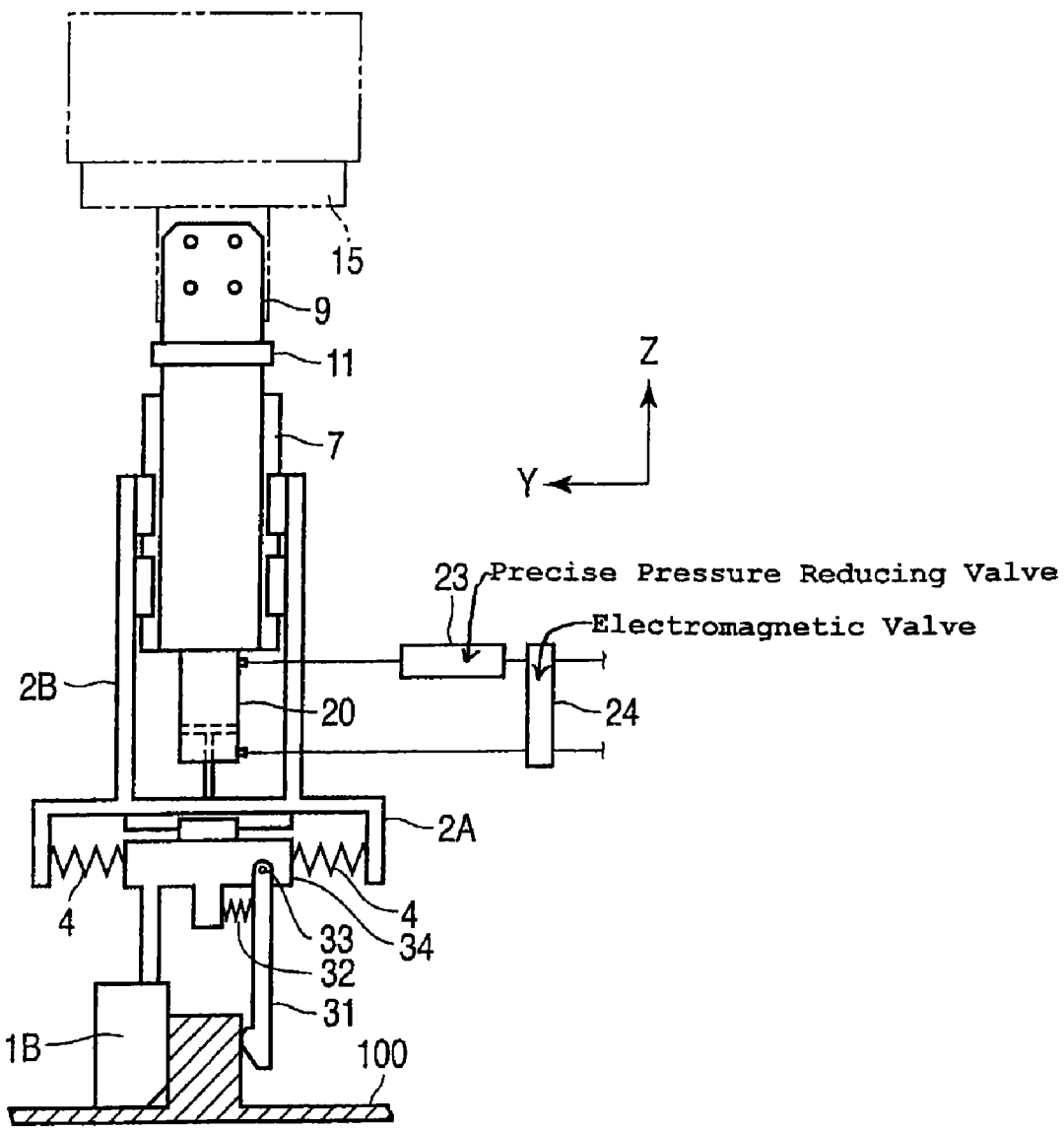
FIG. 2 is a front view showing a structure of a copying apparatus according to a first modification of the first embodiment of the present invention.
Figure 3:
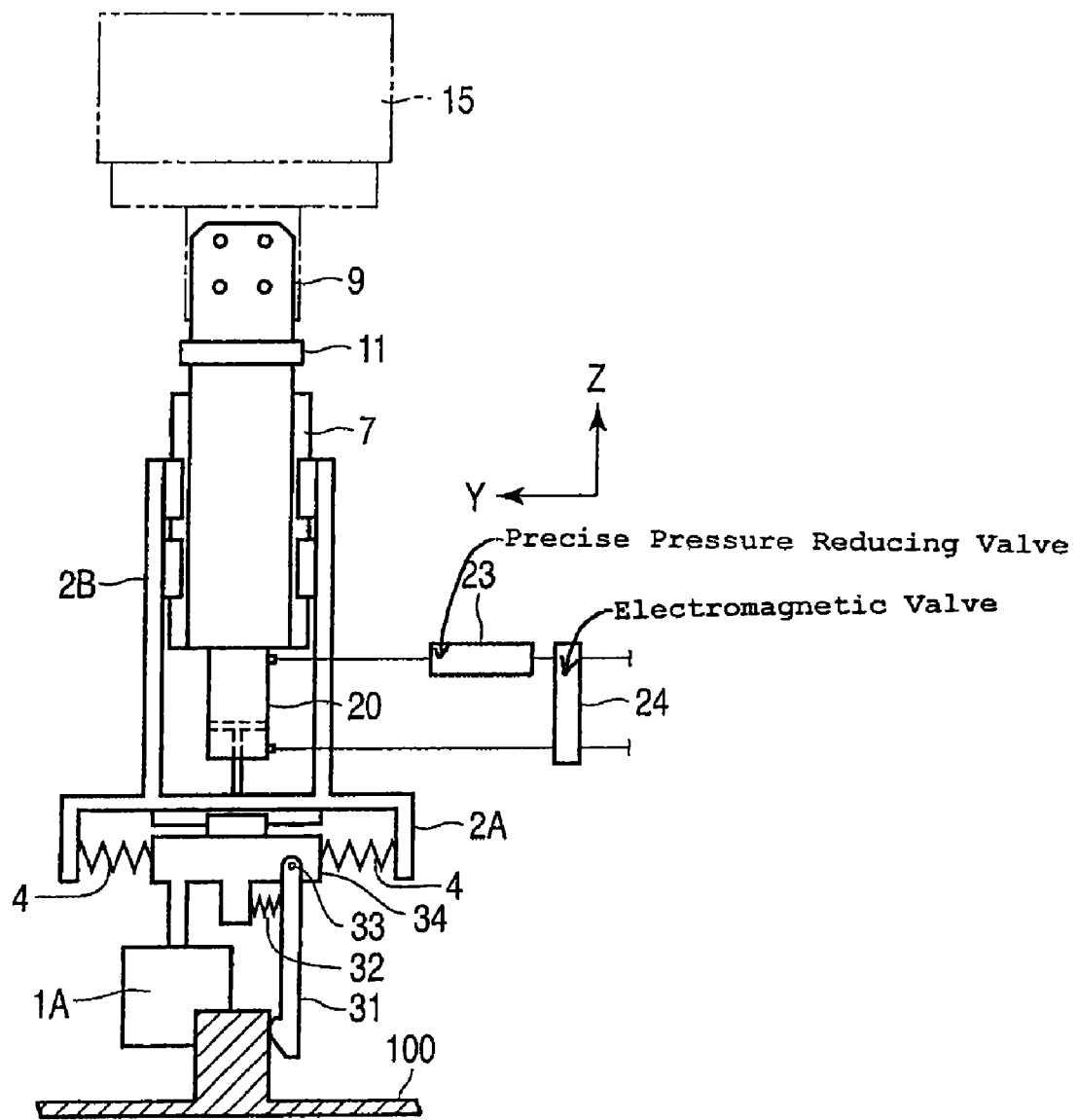
FIG. 3 is a front view showing a structure of a copying apparatus according to a second modification of the first embodiment of the present invention.

As a modification of the first embodiment, as shown in FIGS. 2 and 3, one contact shoe 31 may be an arm having a shape to which the shoe 1 is disposed. Additionally, the shoe may be the rectangular parallelepiped shoe 1A that is parallel to the workpiece 100, the rectangular parallelepiped shoe 1B that is partially notched to fit on the workpiece, or a shoe having any other shape. As a result, there can be provided a copying apparatus suitable for copying a side surface, a bottom surface, or a corner portion (a corner portion may have an R shape) of the workpiece 100. Even in such a copying apparatus according to such a modification, a function as a clamping mechanism is not changed, and the same effect of tolerating displacement as that in the first embodiment can be obtained. Such a modification can have the same structure even in a copying apparatus according to a different embodiment.

In the second embodiment to the fifth embodiment, a degree of freedom in movement of the shoe 1 is added to allow, e.g., oscillation of the shoe, the structures in these embodiments can be freely combined. As a result, there can be provided a copying apparatus that can copy a workpiece while absorbing, e.g., a control error of the feeder or a workpiece disposal error.

In the first embodiment and the eighth embodiment, the description has been given as to the structure where the four or two copying apparatuses 10 are connected, but the present invention is not restricted thereto. The number of the copying apparatuses 10 connected to copy the workpiece 100 is arbitrary. Alternatively, a single copying apparatus 10 may copy the workpiece 100.

In the sixth embodiment, the description has been given as to a structure where an electric signal is used to change the air pressure of the precise pressure reducing valve 83, but a method of utilizing a precise pressure reducing valve which does not use an electric signal or a general pressure reducing valve to manually effect adjustment as required may be adopted.

In the seventh embodiment, the displacement sensors 51 and 52 may not continuously effect measurement, differing from a differential transformer type, and they may instead detect, e.g., ON/OFF. For example, a dog may be used in place of the movable cores 512 and 522, and a proximity sensor may be adopted in place of the differential transformer portions 511 and 521.

Based on the above-explained structure, when the dog and the sensor perform relative motion, the control device that controls the feeder and other parts detects ON or OFF. At this time, it is assumed that FIG. 12B shows an OFF state of the proximity sensor and FIG. 12A shows an ON state of the same. That is, such a sensor detects an appropriate copying range as ON and a situation exceeding the copying range as OFF. If the proximity sensor becomes OFF beyond the appropriate copying range, it means that the copying range is inappropriate. Therefore, it is sufficient to restore the feeder 15 to the appropriate copying range, as in the above description. Such an appropriate copying range can be determined with, e.g., a margin of a stroke of the copying apparatus 10F. Furthermore, one or both of the displacement sensors 51 and 52 can be used as required. Moreover, the disposal positions and the number of the displacement sensors 51 and 52 are not restricted to those in the embodiment.

In the eighth embodiment, although a description has been given as to the sensor 30 as a non-contact type sensor, the sensor 30 does not have to be restricted to the non-contact type, and a contact type can be used as long as the above-described functions are obtained. Moreover, a disposal position or number of the sensors is not restricted, and sensors can be disposed at a position where a workpiece end portion or an interferer can be detected.

In the ninth embodiment, although the ultrasonic flaw detection apparatus using the copying apparatus 10 according to the first embodiment as a basic structure has been described, the copying apparatus according to one of the second embodiment to the eighth embodiment can be used as a basic structure. Additionally, a copying apparatus having a structure obtained by combining these embodiments can be used as the basic structure. Based on such a structure, there can be provided an ultrasonic flaw detection apparatus that can obtain the functions and effects of the copying apparatus according to each embodiment. For example, such an ultrasonic flaw detection apparatus can absorb, e.g., a control error in an up-and-down direction caused by the feeder 15 by using the air cylinder 20. Further, exploiting the functions of the clamping mechanism 3 or the arc slide guides 19A and 19B enables performing ultrasonic flaw detection while absorbing an error of control or disposal position.

In the 10th embodiment, although the ultrasonic flaw detection method using the copying apparatus 10UB according to the ninth embodiment has been described, this method can be likewise applied to the copying apparatus according to any other embodiment. Furthermore, the method can be likewise basically applied to a copying apparatus formed by combining structures according to the plurality of embodiments. Fundamentally, the method can be applied in the same manner. When these copying apparatuses are used to carry out flaw detection based on this ultrasonic flaw detection method, flaw detection can be performed while obtaining the functions and effects of the copying apparatus according to each embodiment.

Although the example where the workpiece is present on the lower side of the copying apparatus has been explained in each embodiment, the copying apparatus may be used sideways or downward. Moreover, for ease of understanding, the description has been given as to the situation where the workpiece is provided on the lower side also in the structure of the copying apparatus. Therefore, when the copying apparatus is used sideways or downward, movement of each portion constituting the copying apparatus becomes associated with this conformation of use. For example, the vertical direction when assuming the workpiece is provided on the lower side is associated with movement in the horizontal direction when the copying apparatus is used sideways.

It is to be noted that the present invention is not restricted to the foregoing embodiments, and constituent elements can be modified and changed into shapes without departing from the scope of the invention at an embodying stage. Additionally, various inventions can be formed by appropriately combining a plurality of constituent elements disclosed in the foregoing embodiments. For example, several constituent elements may be eliminated from all constituent elements disclosed in the embodiments. Further, constituent elements in the different embodiments may be appropriately combined.

What is claimed is:

1. A copying apparatus that copies a workpiece, comprising:
   a first shoe that is brought into contact with a portion of the workpiece to be copied;
   a first air cylinder that enables moving the first shoe in a vertical direction;
   a contact shoe that is inwardly urged to grasp the portion of the workpiece to be copied from side surfaces with respect to a traveling direction in which the workpiece is copied; and
   a sliding unit that slides the contact shoe in a direction orthogonal to the traveling direction in which the workpiece is copied.

2. The apparatus according to claim 1, further comprising:
   a moving unit that enables moving the first shoe as one or more of a pitching movement, rolling movement, and yawing movement with respect to a copying direction.

3. The apparatus according to claim 1, further comprising:
   a turning unit that is provided closer to the first shoe than the first air cylinder, and turns the first shoe accurately, using, as an axis of turning, a point on a plane where the first shoe comes into contact with the portion of the workpiece to be copied.

4. The apparatus according to claim 1, further comprising:
   a second air cylinder that generates a force that is used by the contact shoe to grasp the portion of the workpiece to be copied.

5. The apparatus according to claim 1, further comprising:
   an interferer detector to detect an interferer present on the workpiece in a copying direction,
   wherein the first shoe is made to avoid the interferer based on detection of the interferer by the interferer detector.

6. The apparatus according to claim 1, further comprising:
   a displacement detector to detect displacement of the portion of the workpiece to be copied from a reference position when the first shoe is in contact with the workpiece,
   wherein the portion of the workpiece to be copied is placed in a predetermined copying range based on detection of displacement by the displacement detector.

7. An ultrasonic flaw detection apparatus comprising:
   the copying apparatus according to claim 1; and
   an ultrasonic flaw detector that is provided to the first shoe and generates an ultrasonic wave to the portion of the workpiece to be copied to detect flaws.

8. An ultrasonic flaw detection apparatus comprising:
   the copying apparatus according to claim 2; and
   an ultrasonic flaw detector that is provided to the first shoe and generates an ultrasonic wave to the portion of the workpiece to be copied to detect flaws.

9. An ultrasonic flaw detection apparatus comprising:
   the copying apparatus according to claim 3; and
   an ultrasonic flaw detector that is provided to the first shoe and generates an ultrasonic wave to the portion of the workpiece to be copied to detect flaws.

10. An ultrasonic flaw detection apparatus comprising:
    the copying apparatus according to claim 4; and
    an ultrasonic flaw detector that is provided to the first shoe and generates an ultrasonic wave to the portion of the workpiece to be copied to detect flaws.

11. An ultrasonic flaw detection apparatus comprising:
    the copying apparatus according to claim 5; and
    an ultrasonic flaw detector that is provided to the shoe and generates an ultrasonic wave to the portion of the workpiece to be copied to detect flaws.

12. An ultrasonic flaw detection apparatus comprising:
    the copying apparatus according to claim 6; and
    an ultrasonic flaw detector that is provided to the first shoe and generates an ultrasonic wave to the portion of the workpiece to be copied to detect flaws.

13. An ultrasonic flaw detection method that uses the ultrasonic flaw detection apparatus according to claim 7 to carry out ultrasonic flaw detection with respect to a protruding object placed on an inner peripheral side of a workpiece having a ring shaped, comprising:
    determining an axis on which the workpiece is rotated in a rotation direction of the cross section as a rotation axis $\theta$, an axis that is parallel to the rotation axis $\theta$ and on which the ultrasonic flaw detection apparatus is rotated as a rotation axis $\alpha$, a height of the ultrasonic flaw detection apparatus in an ultrasonic flaw detecting state as L, and an axis running through a rotation center of the rotation axis $\theta$ in a direction running through the cross section as a Z axis;
    obtaining an angle $\theta 1$ formed between a straight line connecting a point having the height L in a normal line direction from the protruding object with the rotation center of the rotation axis $\theta$ and the Z axis;
    rotating the workpiece on the rotation axis $\theta$ at the angle $\theta 1$;
    determining a point where the point having the height L in the normal line direction from the protruding object is provided on the Z axis by the rotation as a point P, and obtaining an angle $\theta 2$ formed between a straight line connecting the point P with the protruding object and the Z axis;
    rotating the ultrasonic flaw detection apparatus on the rotation axis $\alpha$ to cause an angle between the ultrasonic flaw detection apparatus and the Z axis to become the angle $\theta 2$;
    moving the ultrasonic flaw detection apparatus along the Z axis to cause the rotation center of the rotation axis $\alpha$ to overlap the point P; and
    bringing the first shoe into contact by using the first air cylinder.

14. An ultrasonic flaw detection method that uses the ultrasonic flaw detection apparatus according to claim 8 to carry out ultrasonic flaw detection with respect to a protruding object placed on an inner peripheral side of a workpiece having a ring shaped, comprising:
    determining an axis on which the workpiece is rotated in a rotation direction of the cross section as a rotation axis $\theta$, an axis that is parallel to the rotation axis $\theta$ and on which the ultrasonic flaw detection apparatus is rotated as a rotation axis $\alpha$, a height of the ultrasonic flaw detection apparatus in an ultrasonic flaw detecting state as L, and an axis running through a rotation center of the rotation axis θ in a direction running through the cross section as a Z axis;

obtaining an angle θ1 formed between a straight line connecting a point having the height L in a normal line direction from the protruding object with the rotation center of the rotation axis θ and the Z axis;

rotating the workpiece on the rotation axis θ at the angle θ1;

determining a point where the point having the height L in the normal line direction from the protruding object is provided on the Z axis by the rotation as a point P, and obtaining an angle θ2 formed between a straight line connecting the point P with the protruding object and the Z axis;

rotating the ultrasonic flaw detection apparatus on the rotation axis α to cause an angle between the ultrasonic flaw detection apparatus and the Z axis to become the angle θ2;

moving the ultrasonic flaw detection apparatus along the Z axis to cause the rotation center of the rotation axis α to overlap the point P; and bringing the first shoe into contact by using the first air cylinder.

15. An ultrasonic flaw detection method that uses the ultrasonic flaw detection apparatus according to claim 9 to carry out ultrasonic flaw detection with respect to a protruding object placed on an inner peripheral side of a workpiece having a ring shaped, comprising:

determining an axis on which the workpiece is rotated in a rotation direction of the cross section as a rotation axis θ, an axis that is parallel to the rotation axis θ and on which the ultrasonic flaw detection apparatus is rotated as a rotation axis α, a height of the ultrasonic flaw detection apparatus in an ultrasonic flaw detecting state as L, and an axis running through a rotation center of the rotation axis θ in a direction running through the cross section as a Z axis;

obtaining an angle θ1 formed between a straight line connecting a point having the height L in a normal line direction from the protruding object with the rotation center of the rotation axis θ and the Z axis;

rotating the workpiece on the rotation axis θ at the angle θ1;

determining a point where the point having the height L in the normal line direction from the protruding object is provided on the Z axis by the rotation as a point P, and obtaining an angle θ2 formed between a straight line connecting the point P with the protruding object and the Z axis;

rotating the ultrasonic flaw detection apparatus on the rotation axis α to cause an angle between the ultrasonic flaw detection apparatus and the Z axis to become the angle θ2;

moving the ultrasonic flaw detection apparatus along the Z axis to cause the rotation center of the rotation axis α to overlap the point P; and bringing the first shoe into contact by using the first air cylinder.

16. An ultrasonic flaw detection method that uses the ultrasonic flaw detection apparatus according to claim 10 to carry out ultrasonic flaw detection with respect to a protruding object placed on an inner peripheral side of a workpiece having a ring shaped, comprising:

determining an axis on which the workpiece is rotated in a rotation direction of the cross section as a rotation axis θ, an axis that is parallel to the rotation axis θ and on which the ultrasonic flaw detection apparatus is rotated as a rotation axis α, a height of the ultrasonic flaw detection apparatus in an ultrasonic flaw detecting state as L, and an axis running through a rotation center of the rotation axis θ in a direction running through the cross section as a Z axis;

obtaining an angle θ1 formed between a straight line connecting a point having the height L in a normal line direction from the protruding object with the rotation center of the rotation axis θ and the Z axis;

rotating the workpiece on the rotation axis θ at the angle θ1;

determining a point where the point having the height L in the normal line direction from the protruding object is provided on the Z axis by the rotation as a point P, and obtaining an angle θ2 formed between a straight line connecting the point P with the protruding object and the Z axis;

rotating the ultrasonic flaw detection apparatus on the rotation axis α axis α to cause an angle between the ultrasonic flaw detection apparatus and the Z axis to become the angle θ2;

moving the ultrasonic flaw detection apparatus along the Z axis to cause the rotation center of the rotation axis α to overlap the point P; and bringing the first shoe into contact by using the first air cylinder.

17. An ultrasonic flaw detection method that uses the ultrasonic flaw detection apparatus according to claim 11 to carry out ultrasonic flaw detection with respect to a protruding object placed on an inner peripheral side of a workpiece having a ring shaped, comprising:

determining an axis on which the workpiece is rotated in a rotation direction of the cross section as a rotation axis θ, an axis that is parallel to the rotation axis θ and on which the ultrasonic flaw detection apparatus is rotated as a rotation axis α, a height of the ultrasonic flaw detection apparatus in an ultrasonic flaw detecting state as L, and an axis running through a rotation center of the rotation axis θ in a direction running through the cross section as a Z axis;

obtaining an angle θ1 formed between a straight line connecting a point having the height L in a normal line direction from the protruding object with the rotation center of the rotation axis θ and the Z axis;

rotating the workpiece on the rotation axis θ at the angle θ1;

determining a point where the point having the height L in the normal line direction from the protruding object is provided on the Z axis by the rotation as a point P, and obtaining an angle θ2 formed between a straight line connecting the point P with the protruding object and the Z axis;

rotating the ultrasonic flaw detection apparatus on the rotation axis α to cause an angle between the ultrasonic flaw detection apparatus and the Z axis to become the angle θ2;

moving the ultrasonic flaw detection apparatus along the Z axis to cause the rotation center of the rotation axis α to overlap the point P; and bringing the first shoe into contact by using the first air cylinder.

18. An ultrasonic flaw detection method that uses the ultrasonic flaw detection apparatus according to claim 12 to carry out ultrasonic flaw detection with respect to a protruding object placed on an inner peripheral side of a workpiece having a ring shaped, comprising:

determining an axis on which the workpiece is rotated in a rotation direction of the cross section as a rotation axis $\theta$, an axis that is parallel to the rotation axis $\theta$ and on which the ultrasonic flaw detection apparatus is rotated as a rotation axis $\alpha$, a height of the ultrasonic flaw detection apparatus in an ultrasonic flaw detecting state as L, and an axis running through a rotation center of the rotation axis $\theta$ in a direction running through the cross section as a Z axis;

obtaining an angle $\theta 1$ formed between a straight line connecting a point having the height L in a normal line direction from the protruding object with the rotation center of the rotation axis $\theta$ and the Z axis;

rotating the workpiece on the rotation axis $\theta$ at the angle $\theta 1$;

determining a point where the point having the height L in the normal line direction from the protruding object is provided on the Z axis by the rotation as a point P, and obtaining an angle $\theta 2$ formed between a straight line connecting the point P with the protruding object and the Z axis;

rotating the ultrasonic flaw detection apparatus on the rotation axis $\alpha$ to cause an angle between the ultrasonic flaw detection apparatus and the Z axis to become the angle $\theta 2$;

moving the ultrasonic flaw detection apparatus along the Z axis to cause the rotation center of the rotation axis $\alpha$ to overlap the point P; and bringing the first shoe into contact by using the first air cylinder.

* * * * *